United States Patent [19]

Baylis et al.

[11] Patent Number: 5,051,524

[45] Date of Patent: Sep. 24, 1991

[54] SUBSTITUTED PROPANE-PHOSPHINIC ACID COMPOUNDS

[75] Inventors: Eric K. Baylis, Stockport, England; Helmut Bittiger, Freiburg, Fed. Rep. of Germany; Wolfgang Fröstl, Basle, Switzerland; Roger G. Hall, Flixton, England; Ludwig Maier, Arlesheim, Switzerland; Stuart J. Mickel, Lausen, Switzerland; Hans-Rudolf Olpe, Bottmingen, Switzerland

[73] Assignee: Ciba-Geigy Corporation, Ardsley, N.Y.

[21] Appl. No.: 484,716

[22] Filed: Feb. 26, 1990

Related U.S. Application Data

[63] Continuation-in-part of Ser. No. 378,887, Jul. 12, 1989, which is a continuation-in-part of Ser. No. 275,882, Nov. 25, 1988, abandoned.

[30] Foreign Application Priority Data

Dec. 4, 1987 [GB] United Kingdom ................. 8728483

[51] Int. Cl.$^5$ .............................................. C07F 9/48
[52] U.S. Cl. ...................................... 558/145; 558/87
[58] Field of Search ................................... 558/145, 87

[56] References Cited

U.S. PATENT DOCUMENTS

| | | | |
|---|---|---|---|
| 3,184,496 | 5/1965 | Baranauckas et al. | 562/8 |
| 4,064,163 | 12/1977 | Drach et al. | 562/25 |
| 4,536,355 | 8/1985 | Lee et al. | 260/944 |
| 4,618,358 | 10/1986 | Maier | 71/86 |
| 4,656,298 | 4/1987 | Dingwall et al. | 556/12 |

FOREIGN PATENT DOCUMENTS

| | | |
|---|---|---|
| 181833 | 5/1986 | European Pat. Off. . |
| 356128 | 2/1990 | European Pat. Off. . |
| 1351503 | 5/1974 | United Kingdom . |

OTHER PUBLICATIONS

Phosphorous and Sulfur, vol. 18, pp. 353-356 (1983).

Chemical Abstracts 97:72585v (1982).

Primary Examiner—J. E. Evans
Attorney, Agent, or Firm—JoAnn Villamizar

[57] ABSTRACT

Compounds of the formula I

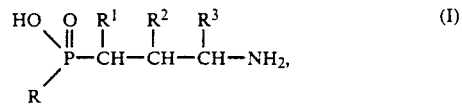

wherein R denotes an aliphatic, cycloaliphatic, cycloaliphatic-aliphatic or araliphatic radical having 2 or more carbon atoms, and wherein one of the groups $R^1$, $R^2$ and $R^3$ represents hydrogen or an aliphatic, cycloaliphatic, araliphatic or aromatic radical, another one of $R^1$, $R^2$ and $R^3$ is hydrogen or, in the case of $R^1$ and $R^2$, is hydroxy, and the remaining one of $R^1$, $R^2$ and $R^3$ is hydrogen, or wherein R denotes methyl, $R_1$ denotes hydrogen or hydroxy, $R_2$ denotes an aromatic radical and $R_3$ represents hydrogen, and their salts have GABA$_B$-antagonistic properties and can be used as GABA$_B$-antagonists. They are obtained when in a compound of formula II

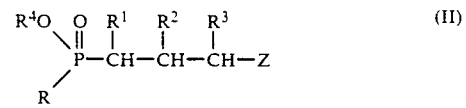

in which R, $R^1$, $R^2$ and $R^3$ have their previous significances, Z represents —NH$_2$ and $R^4$ denotes a hydroxy-protective group $R^5$ or, when $R^1$ and $R^3$ denote hydrogen and $R^2$ denotes hydrogen or alkyl, denotes an alkali metal or ammonium ion $R^6$, or Z represents a protected or latent amino group Z° and $R^4$ denotes hydrogen or a hydroxy-protective group $R^5$, any group $R^5$ or $R^6$ is replaced by hydrogen, and/or any group Z° is converted into —NH$_2$.

1 Claim, No Drawings

SUBSTITUTED PROPANE-PHOSPHINIC ACID COMPOUNDS

This is a continuation-in-part application of our copending patent application Ser. No. 378,887, filed July 12, 1989 which in turn is a continuation-in-part of our previous patent application Ser. No. 275,882, filed Nov. 25, 1988 now abandoned.

The invention relates to compounds of the formula I

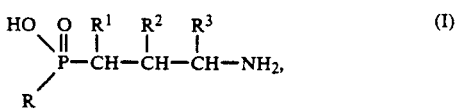

wherein R denotes an aliphatic, cycloaliphatic, cycloaliphatic-aliphatic or araliphatic radical having 2 or more carbon atoms, and wherein one of the groups $R^1$, $R^2$ and $R^3$ represents hydrogen or an aliphatic, cycloaliphatic, araliphatic or aromatic radical, another one of $R^1$, $R^2$ and $R^3$ is hydrogen or, in the case of $R^1$ and $R^2$ is hydroxy, and the remaining one of $R^1$, $R^2$ and $R^3$ is hydrogen, or wherein R denotes methyl, $R_1$ denotes hydrogen or hydroxy, $R_2$ denotes an aromatic radical and $R_3$ represents hydrogen, and to their pharmaceutically acceptable salts for use for the treatment of the human or animal body, to pharmaceutical compositions containing the same and to compounds of the formula I, with the proviso that R is different from 1,1-di($C_1$–$C_4$-alkoxy)-$C_1$–$C_5$-alkyl, if one of $R^1$, $R^2$ and $R^3$ represents hydrogen, $C_1$–$C_8$-alkyl, $C_3$–$C_6$-cycloalkyl, phenyl optionally substituted by halogen, $C_1$–$C_4$-alkyl, $C_1$–$C_4$-alkoxy and/or trifluoromethyl or $C_7$–$C_{10}$-phenylalkyl optionally substituted in the phenyl moiety by halogen, $C_1$–$C_4$-alkyl, $C_1$–$C_4$-alkoxy and/or trifluoromethyl and the other two of $R^1$, $R^2$ and $R^3$ are hydrogen, and with the additional proviso that R is different from ethyl if $R^2$ represents hydroxy and $R^1$ and $R^2$ are hydrogen, and to their salts, provided that salts of compounds of the formula I, wherein R denotes an unsubstituted aliphatic, cycloaliphatic or araliphatic hydrocarbon radical, $R^1$ and $R_3$ denote hydrogen and $R^2$ is hydrogen or alkyl, with bases are different from alkali metal and ammonium salts, and to a process for their manufacture.

Aliphatic radicals R are, for example, alkyl groups that may be interrupted by one or two mutually spaced atoms selected from oxygen and sulfur and/or substituted by halogen or hydroxy, such as alkyl, alkyl mono-, di- or poly- substituted by halogen and/or hydroxy, alkyl being interrupted by one or two mutually spaced atoms selected from oxygen and sulfur or alkyl being interrupted by one or two mutually spaced atoms selected from oxygen and sulfur and substituted by halogen and/or hydroxy, alkenyl groups that may be mono-, di- or poly- substituted by halogen and/or hydroxy, such as lower alkenyl or lower alkenyl substituted by halogen and/or hydroxy, or alkynyl groups, such as lower alkynyl. Aliphatic radicals $R_1$, $R_2$ or $R_3$ are, for example, lower alkyl groups.

Cycloaliphatic radicals R are, for example, cycloalkyl groups that may be interrupted by one or two mutually spaced atoms selected from oxygen and sulfur and/or substituted by hydroxy, such as cycloalkyl, cycloalkyl being interrupted by one or two mutually spaced atoms selected from oxygen and sulfur or cycloalkyl substituted by hydroxy. Cycloaliphatic radicals $R_1$, $R_2$ or $R_3$ are, for example, cycloalkyl groups.

Cycloaliphatic-aliphatic radicals R are, for example, cycloalkyl-lower alkyl groups that may be interrupted by one or two mutually spaced atoms selected from oxygen and sulfur and/or substituted by hydroxy and/or lower alkylthio, such as cycloalkyl-lower alkyl, cycloalkyl-lower alkyl being interrupted by one or two mutually spaced atoms selected from oxygen and sulfur or cycloalkyl-lower alkyl substituted in the cycloalkyl moiety by hydroxy or lower alkylthio and/or in the alkylene moiety by hydroxy.

Araliphatic radicals R and/or $R_1$, $R_2$ or $R_3$ are, for example, phenyl-lower alkyl or naphthyl-lower alkyl radicals that may be substituted in the aryl ring by halogen, lower alkyl, lower alkoxy and/or trifluoromethyl and/or in the lower alkylene moiety by hydroxy, such as phenyl-lower alkyl, phenyl-(1-hydroxy)-lower alkyl, naphthyl-lower alkyl or phenyl-lower alkyl substituted in the phenyl moiety by halogen, lower alkyl, lower alkoxy and/or trifluoromethyl.

Aromatic radicals $R_1$, $R_2$ or $R_3$ are, for example, phenyl, naphthyl or phenyl substituted by halogen, lower alkyl, lower alkoxy and/or trifluoromethyl.

In compounds of formula I the group R is bonded to the P-atom via a carbon atom.

Alkyl, alkenyl and alkynyl R may contain up to and including 14, preferably 12 carbon atoms and are represented by lower alkyl, lower alkenyl and lower alkynyl. Alkyl R may also be a $C_8$–$C_{14}$-, e.g. a $C_8$–$C_{12}$-alkyl, such as an octyl, nonyl, decyl, undecyl or dodecyl group, e.g. a decyl or dodecyl group.

Alkyl or alkenyl mono-, di- or poly- substituted by halogen and/or hydroxy is represented by mono- or dihydroxy-lower alkyl, hydroxy-lower alkenyl, mono-, di- or polyhalogeno-lower alkyl, mono-, di- or polyhalogeno-lower alkenyl, mono-, di- or polyhalogeno-lower hydroxyalkyl and mono-, di- or polyhalogeno-lower hydroxyalkenyl.

Alkyl being interrupted by one or two atoms selected from oxygen and sulfur is represented by lower alkoxy-lower alkyl, lower alkylthio-lower alkyl, lower alkanesulfinyl-lower alkyl, lower alkanesulfonyl-lower alkyl, lower alkoxy-lower alkoxy-lower alkyl, di-lower alkoxy-lower alkyl, di-lower alkylthio-lower alkyl, and lower alkoxy-lower alkylthio-lower alkyl.

Alkyl being interrupted by one or two atoms selected from oxygen and sulphur and substituted by hydroxy and/or halogen is represented by lower alkoxy-(hydroxy)lower alkyl and lower alkoxy-(halogeno)lower alkyl.

Cycloalkyl is represented by $C_3$–$C_8$-cycloalkyl.

Cycloalkyl substituted by hydroxy is represented by 1-hydroxy-$C_3$–$C_8$-cycloalkyl.

Cycloalkyl and cycloalkyl in cycloalkyl-lower alkyl, in either case, being interrupted by one or two atoms selected from oxygen and sulfur is represented by oxa-$C_3$–$C_8$-cycloalkyl, thia-$C_3$–$C_8$-cycloalkyl, dioxa-$C_3$–$C_8$-cycloalkyl, dithia-$C_3$–$C_8$-cycloalkyl and oxathia-$C_3$–$C_8$-cycloalkyl.

Cycloalkyl-lower alkyl substituted in the cycloalkyl moiety by hydroxy and/or lower alkylthio and/or in the alkylene moiety by hydroxy is represented by lower alkylthiocycloalkyl-lower alkyl, cycloalkyl(hydroxy)-lower alkyl and lower alkylthiocycloalkyl-(hydroxy)-lower alkyl.

The general definitions used herein have the following meaning within the scope of the present invention.

The term "lower" referred to above and hereinafter in connection with organic radicals or compounds respectively, if not defined explicitly otherwise, defines such with up to and including 7, preferably up to and including 4, carbon atoms.

Lower alkyl R is represented by $C_2$–$C_7$-alkyl, especially by $C_3$–$C_7$-alkyl, e.g. propyl, isopropyl, butyl, isobutyl, sec.-butyl, tert.-butyl, (2-methyl)butyl, hexyl or heptyl. Lower alkyl other than R denotes, for example, $C_1$–$C_4$-alkyl, e.g. methyl, ethyl, propyl, isopropyl, butyl or tert.-butyl.

Lower alkenyl denotes, for example, $C_3$–$C_7$-alkenyl, preferably $C_3$–$C_5$-alkenyl, carrying the double bond in a higher than the $\alpha,\beta$-position, and is e.g. 2-propenyl (allyl), but-3-en-1-yl, (2-methyl)prop-2-en-1-yl (isobutenyl) or (5-methyl)but-2-en-1-yl, but may also carry the double bond in $\alpha,\beta$-position and may be, for example, vinyl, prop-1-enyl or but-1-enyl, or may be a $C_6$- or $C_7$-alkenyl, such as a hexenyl or heptenyl, group.

Lower alkynyl denotes, for example, $C_3$–$C_7$-alkynyl, preferably $C_3$–$C_5$-alkynyl, carrying the triple bond in a higher than the $\alpha,\beta$-position and is e.g. 2-propynyl (propargyl), but-3-yn-1-yl, but-2-yn-1-yl or pent-3-yn-1-yl.

$C_3$–$C_8$Cycloalkyl preferably has 3 to 6 ring carbon atoms and thus is $C_3$–$C_6$-cycloalkyl, e.g. cyclopropyl, cyclobutyl, cyclopentyl or cyclohexyl.

$C_3$–$C_8$-Cycloalkyl-lower alkyl preferably has 3 to 6 ring and 1 to 4 chain carbon atoms and is, for example, $C_3$–$C_6$-cycloalkyl-$C_1$–$C_4$-alkyl, such as cyclopropylmethyl, cyclobutylmethyl or cyclohexylmethyl.

Mono- or dihydroxy-lower alkyl preferably carries one of the hydroxy groups in $\alpha$-position and is for example, $\alpha$-hydroxy-$C_2$–$C_7$-alkyl, such as $\alpha$-hydroxy-$C_2$–$C_4$-alkyl, e.g. 1-hydroxyethyl, 2-(2-hydroxy)propyl, 1-hydroxybutyl, 2-(2-hydroxy)butyl or 1-(1-hydroxy-2-methyl)propyl, or $\alpha,\beta$-dihydroxy-$C_2$–$C_7$-alkyl, such as 1,2-dihydroxy-prop-2-yl, but may also carry a single hydroxy group in a higher than the $\alpha$-position and denote, for example, $\beta$-, $\gamma$- or $\delta$-hydroxy-$C_2$–$C_7$-alkyl, e.g. 3-hydroxypropyl or 2-, 3-or 4-hydroxybutyl.

Hydroxy-lower alkenyl preferably carries the hydroxy group in $\alpha$-position and the double bond in a higher than the $\alpha,\beta$-position and is, for example, corresponding $\alpha$-hydroxy-$C_3$–$C_5$-alkenyl, e.g. 1-hydroxybut-2-enyl.

Mono-, di- or polyhalogeno-lower alkyl is for example, mono-, di- or trifluoro-$C_2$–$C_5$-alkyl, e.g. 3,3,3-trifluoropropyl, 4,4,4-trifluorobutyl, 1- or 2-fluorobutyl or 1,1-difluorobutyl.

Mono-, di- or polyhalogeno-lower alkenyl is, for example, mono-, di- or trifluoro-$C_3$–$C_5$-alkenyl, e.g. 2-fluorobut-2-enyl.

Mono-, di- or polyhalogeno-lower hydroxyalkyl and mono-, di- or poly- halogeno-lower hydroxyalkenyl preferably carries the hydroxy group in $\alpha$-position and the halogen atom(s) in a higher than the $\alpha$-position and is, for example, corresponding mono-, di- or trifluoro-$\alpha$-hydroxy-$C_2$–$C_7$-alkyl or mono- di- or trifluoro-$C_3$–$C_7$-alkenyl, e.g. 2-fluoro-1-hydroxy-butyl, 2-fluoro-1-hydroxy-but-2-en-1-yl or 4,4,4-trifluoro-1-hydroxybutyl.

Lower alkoxy-lower alkyl preferably has up to 10 carbon atoms and is, for example, $C_1$–$C_4$-alkoxy-$C_1$–$C_4$-alkyl, such as $C_1$–$C_3$-alkoxy-$C_1$–$C_3$-alkyl, e.g. methoxymethyl, ethoxymethyl, 2-methoxyethyl, 2-ethoxyethyl, 3-methoxypropyl or 1- or 2-methoxybutyl.

Lower alkoxy is, for example, $C_1$–$C_4$-alkoxy, e.g. methoxy, ethoxy, isopropoxy, propoxy, butoxy, sec.-butoxy or tert.-butoxy.

Lower alkoxy-lower alkoxy-lower alkyl is, for example, $C_1$–$C_4$-alkoxy-$C_2$–$C_4$-alkoxy-$C_1$–$C_4$-alkyl, e.g. 2-methoxyethoxymethyl.

Lower alkylthio-lower alkyl preferably has up to 10 carbon atoms and is, for example, $C_1$–$C_4$-alkylthio-$C_1$–$C_4$-alkyl, such as $C_1$–$C_3$-alkylthio-$C_1$–$C_3$-alkyl, e.g. methylthiomethyl, ethylthiomethyl, 2-methylthioethyl, 2-ethylthioethyl or 3-methylthiopropyl.

Lower alkanesulfinyl- and lower alkanesulfonyl-lower alkyl preferably has up to 10 carbon atoms and is, for example, $C_1$–$C_4$-alkanesulfinyl- or $C_1$–$C_4$-alkanesulfonyl-$C_1$–$C_4$-alkyl; e.g. ethanesulfinylmethyl or ethanesulfonylmethyl.

Di-lower alkoxy-lower alkyl preferably has up to 15 carbon atoms totally and is, for example, di-$C_1$–$C_4$-alkoxy-$C_1$–$C_3$-alkyl, such as di-$C_1$–$C_3$-alkoxy-$C_1$–$C_3$-alkyl, e.g. dimethoxymethyl, diethoxymethyl, dipropyloxymethyl, 1,1- or 2,2-diethoxyethyl, diisopropyloxymethyl, di-n-butoxymethyl or 3,3-dimethoxypropyl.

Di-lower alkylthio-lower alkyl preferably has up to 15 carbon atoms totally and is, for example, di-$C_1$–$C_4$-alkylthio-$C_1$–$C_4$-alkyl, such as di-$C_1$–$C_3$-alkylthio-$C_1$–$C_3$-alkyl, e.g. dimethylthiomethyl, diethylthiomethyl or 1,1-or 2,2-dimethylthioethyl.

Lower alkoxy-(hydroxy)lower alkyl is, for example $C_1$–$C_4$-alkoxy-$C_1$–$C_7$(hydroxy)alkyl e.g. 2-(2-hydroxy-3-methoxy)propyl.

Lower alkoxy-(halogeno)lower alkyl is, for example $C_1$–$C_4$-alkoxy-$C_1$–$C_7$(halogeno)alkyl e.g. 1-(2-fluoro-1-methoxy)butyl.

Hydroxy-$C_3$–$C_8$-cycloalkyl is, for example, 1-hydroxy-$C_3$–$C_6$-cycloalkyl, e.g. 1-hydroxycyclobutyl.

Oxa- or thia-$C_3$–$C_8$-cycloalkyl preferably has 2 to 6 ring carbon atoms is, for example, 2-oxacyclopropyl (oxiranyl), 2- or 3-oxacyclobutyl (oxetanyl), 2- or 3-thiacyclobutyl (thietanyl), 2- or 3-oxacylcopentyl (tetrahydrofuranyl), 2- or 3-thiacyclopentyl (thiolanyl) or 2-oxacyclohexyl (tetrahydropyranyl).

Dioxa-$C_3$–$C_8$-cycloalkyl preferably has 3 to 5 ring carbon atoms and those two oxygen atoms in 1,3-position to each other, and represents e.g. 1,3-dioxolan-2-yl or 1,3-dioxan-2-yl.

Dithia-$C_3$–$C_8$-cycloalkyl preferably has 3 to 5 ring carbon atoms and carries those two sulfur atoms in 1,3-position to each other and represents e.g. 1,3-dithiolan-2-yl or 1,3-dithioxan-2-yl. Oxathio-$C_3$–$C_8$-cycloalkyl is, for example 1,3-oxathiolan-2-yl or 1,3-oxathioxan-2-yl.

$C_3$–$C_8$-Cycloalkyl-(hydroxy)lower alkyl preferably has 3 to 6 ring and 1 to 4 chain carbon atoms and is, for example, cyclo-$C_3$–$C_6$-alkyl-$C_1$–$C_4$-alkyl, e.g. 1-cyclopropyl-1-hydroxymethyl or 1-hydroxy-1-cyclobutylmethyl. Lower alkylthiocycloalkyl-(hydroxy) lower alkyl is, for example, 1-hydroxy1-(2-methylthiocyclopropyl).

Halogen, as a substituent of aromatic and/or araliphatic radicals $R^1$, $R^2$ or $R^3$, is preferably chloro, but may also be fluoro, bromo or iodo.

A phenyl or naphthyl group may have one or more than one, preferably one or two of the same or different substituents as defined hereinbefore. Phenyl- or naphthyl-lower alkyl is e.g. benzyl, naphth-2-ylmethyl, 1- or 2-phenylethyl or 2- or 3-phenylpropyl, each optionally substituted as described hereinbefore.

Salts of the compounds of the formula I are particularly pharmaceutically acceptable salts thereof, such as the corresponding addition salts with acids, as well as the salts with bases. Suitable acids for the formation of acid addition salts are, for example, mineral acids, such as hydrochloric, hydrobromic, sulphuric or phosphoric acid, or organic acids, such as organic sulphonic acids, for example, benzenesulphonic, 4-toluenesulphonic or methanesulphonic acid, and organic carboxylic acids, such as acetic, lactic, palmitic, stearic, malic, maleic, fumaric, tartaric, ascorbic or citric acid. Salts with bases are, for example, alkali metal or alkaline earth metal salts, such as sodium, potassium, calcium or magnesium salts, or ammonium salts, such as those with ammonia or suitable organic amines, e.g. diethylamine, di-(2-hydroxyethyl)-amine or tri-(2-hydroxyethyl)-amine. The compounds of the formula I may also form inner salts.

Depending on the presence of asymmetric carbon atoms, the compounds of this invention may be in the form of mixtures of isomers, particularly racemates, or in the form of pure isomers, particularly optical antipodes.

Compounds of the formula I, wherein R denotes an 1,1-di($C_1$-$C_4$-alkoxy)-$C_1$-$C_5$-alkyl group, one of $R^1$, $R^2$ and $R^3$ denotes hydrogen, $C_1$-$C_8$-alkyl, $C_3$-$C_6$-cycloalkyl, phenyl optionally substituted by halogen, $C_1$-$C_4$-alkyl, $C_1$-$C_4$-alkoxy and/or trifluoromethyl or $C_7$-$C_{10}$-phenylalkyl optionally substituted in the phenyl moiety by halogen, $C_1$-$C_4$-alkyl, $C_1$-$C_4$-alkoxy and/or trifluoromethyl and the other two are hydrogen, are known as intermediates for the preparation of corresponding compounds, wherein R denotes hydrogen, and of their salts. Also, salts of those compounds of the formula I, wherein R denotes a hydrocarbon radical, $R_1$ and $R_3$ denote hydrogen and $R_2$ denotes hydrogen or alkyl, are known and have been proposed as flame-protective and surface-active agents.

However, compounds of formula I wherein R denotes 1,1-di($C_1$-$C_4$-alkoxy)-$C_1$-$C_5$-alkyl, one of $R^1$ and $R^2$ represents hydroxy and $R^3$ and the other one of $R^1$ and $R^2$ are hydrogen, the specific compounds of formula I, wherein R is diethoxymethyl, one of $R^1$ and $R^2$ is p-chlorophenyl or methyl and the other one and $R^3$ are hydrogen, and compounds of the formula I, wherein R is a group of the formula —CH(OR')$_2$ in which R' represents $C_1$-$C_4$-alkyl, such as ethyl, propyl, isopropyl or n-butyl, and $R^1$, $R^2$ and $R^3$ are hydrogen, and their salts are hitherto not described in the art and are thus considered novel.

The invention therefore relates also to those generically and specifically novel compounds generically known as intermediates and to their pharmaceutically acceptable salts for use in the treatment of the human or animal body and to pharmaceutical preparation containing the same, as well as to compounds of formula I, wherein R is diethoxymethyl, one of $R^1$ and $R^2$ is p-chlorophenyl or methyl and the other one and $R^3$ is hydrogen, or wherein R is a group of the formula —CH(OR')$_2$ in which R' represents $C_1$-$C_4$-alkyl, such as ethyl, propyl, isopropyl or n-butyl, and $R^1$, $R^2$ and $R^3$ denote hydrogen, and to their salts.

It has now been found that the compounds of the formula I and their pharmaceutically acceptable salts possess valuable pharmacological properties. They show an effective binding at the GABA$_B$-receptor and are found to act as antagonists on said receptor. Mechanistically, antagonism at GABA$_B$ receptors may increase the release of fast excitatory amino acid transmitters, i.e glutamate and aspartate, thus improving information processing in the brain. In line with this is the finding that the late inhibitory postsynaptic potential in hippocampus, attributed to a GABA$_B$ mechanism, is shortened by the antagonists thus allowing a faster sequence of nerve impulse transfer.

On the other hand, chronic treatment with antidepressants and repetitive electroshock have been found to increase the number of GABA$_B$ receptors in rat cerebral cortex. In line with receptor theories, chronic treatment with GABA$_B$ antagonists should result in the same effect. For these and other reasons, GABA$_B$ antagonists may therefore act as antidepressants.

The GABA$_B$ antagonists of the present invention interact at the GABA$_B$ receptor with IC$_{50}$ values starting from about $10^{-7}$ M (moles/litre) in rat brain cortex membranes. In contrast to GABA$_B$ agonists, such as baclofen, they do not potentiate the stimulation of adenylate cyclase in rat cerebral cortex slices by noradrenaline, but antagonize the effects of baclofen. The antagonism against baclofen has also been shown in in vitro electrophysiological models, such as the penicilline-induced "epileptic" hippocampal slice preparation, where baclofen, at a concentration of 6 μM inhibits "epileptic"-like discharges of pyramidal cells. The compounds of the invention antagonise the effects of baclofen at concentrations from approximately 10 to approximately 100 μM. In vivo, antagonism has been shown by ionophoresis of baclofen on rat cerebral cortex, and systemic application of antagonists in doses of 10-100 mg/kg. The muscle relaxant effects of baclofen measured in the rotorod model are also antagonized at doses of about 30 mg/kg ip.

The antagonists do not only show antagonistic effects against baclofen, but have, as theoretically expected (see above), also effects on their own as antagonists of endogenous GABA. Thus the antagonists are active in behavioural models which are established in the art to be indicative of antidepressant, anxiolytic and/or nootropic properties. Compounds of the formula I have been found to be active, after peroral application, in the swim test according to Porsolt, in the Geller test, the one trial, step-down passive avoidance test (one-trial modification) in pretrial and posttrial situations, in the two compartment test and in the complex labyrinth. In addition, in studies on Rhesus monkeys, an increase in playfulness, exploration, social grooming and a reduction of signs of anxiety were observed. Accordingly, the compounds of formula I may be used as nootropic, antidepressive and anxiolytic agents. Of course, they may also be used as baclofen-antidotes.

The invention relates in particular to compounds of the formula I, wherein R has 2 or more carbon atoms and denotes alkyl, alkenyl, alkynyl, alkyl or alkenyl mono-, di- or poly-substituted by halogen and/or hydroxy, alkyl being interrupted by one or two mutually spaced atoms selected from oxygen and sulfur, alkyl being interrupted by one or two mutually spaced atoms selected from oxygen and sulfur and substituted by halogen and/or hydroxy, cycloalkyl, cycloalkyl substituted by hydroxy, cycloalkyl being interrupted by one or two mutually spaced atoms selected from oxygen and sulfur, cycloalkyl-lower alkyl, cycloalkyl-lower alkyl substituted in the cycloalkyl moiety by hydroxy or lower alkylthio and/or in the alkylene moiety by hydroxy, cycloalkyl-lower alkyl being interrupted by one or two mutually spaced atoms selected from oxygen and sulfur in the cycloalkyl moiety, phenyl-lower alkyl, naphthyl-lower alkyl or phenyl- or naphthyl lower alkyl ring substituted by halogen, lower alkyl, lower alkoxy and/or trifluoromethyl or naphthyl-lower alkyl, and/or chain-substituted by hydroxy and wherein one of the groups $R^1$, $R^2$ and $R^3$ represents hydrogen, lower alkyl, cycloalkyl, phenyl or naphthyl, phenyl or naphthyl substituted by halogen, lower alkyl, lower alkoxy and/or trifluoromethyl, phenyl-lower alkyl or phenyl lower alkyl substituted in the phenyl moiety by halogen, lower alkyl, lower alkoxy and/or trifluoromethyl, another one of $R^1$, $R^2$ and $R^3$ is hydrogen or, in the case of $R^1$ and $R^2$, is hydroxy and the remaining one of $R^1$, $R^2$ and $R^3$ is hydrogen, and to their salts, especially pharmaceutically acceptable salts, with the provisos given hereinbefore.

The invention relates, for example, to compounds of the formula I, wherein R has 2 or more carbon atoms and is lower alkyl, lower alkenyl, lower alkynyl, alkyl being interrupted by one or two mutually spaced atoms selected from oxygen, sulfur and cycloalkyl, cycloalkyl being interrupted by one or two mutually spaced atoms selected from oxygen and sulfur, cycloalkyl or cycloalkyl-lower alkyl being interrupted by one or two mutually spaced atoms selected from oxygen and sulfur in the cycloalkyl moiety; and wherein one of the groups $R^1$, $R^2$ and $R^3$ represents hydrogen, lower alkyl, cycloalkyl, phenyl, phenyl substituted by halogen, lower alkyl, lower alkoxy and/or trifluoromethyl, phenyl lower alkyl or phenyl lower alkyl substituted in the phenyl moiety by halogen, lower alkyl, lower alkoxy and/or trifluoromethyl, or one of $R^1$ and $R^2$ is hydroxy; and the remaining two of $R^1$, $R^2$ and $R^3$ are hydrogen, and to their salts, especially pharmaceutically acceptable salts, with the provisos given hereinbefore.

The invention relates, above all, to compounds of the formula I, wherein R has 2 or more carbon atoms and is lower alkyl, lower alkenyl, lower alkynyl, a cycloalkyl, hydroxycycloalkyl, cycloalkyl-lower alkyl, cycloalkyl-(hydroxy)lower alkyl or lower alkylthiocycloalkyl-(hydroxy)lower alkyl group having 3 to 6 ring carbon atoms, mono- or dihydroxy-lower alkyl, hydroxy-lower alkenyl, mono-, di- or polyhalogeno-lower alkyl, mono-, di-or polyhalogeno-lower alkenyl, mono-, di- or polyhalogeno-(hydroxy)lower alkyl, mono-, di- or polyhalogeno-(hydroxy)lower alkenyl, lower alkoxy-lower alkyl, lower alkylthio-lower alkyl, lower alkanesulfinyl-lower alkyl, lower alkanesulfonyl-lower alkyl, di-lower alkoxy-lower alkyl, di-lower alkylthio-lower alkyl, lower alkoxyhydroxy)lower alkyl, lower alkoxy-(halogeno)lower alkyl, phenyl-lower alkyl, phenyl-lower alkyl mono- or disubstituted, in the phenyl moiety, by halogen, lower alkyl, lower alkoxy and/or trifluoromethyl, naphthyl-lower alkyl, oxa- or thiacycloalkyl having 2 to 6 ring carbon atoms, or dioxa-, oxathia- or dithiacycloalkyl having 3 to 5 ring carbon atoms, and wherein one of $R^1$, $R^2$, $R^3$ represents hydrogen, lower alkyl, cycloalkyl having 3 to 6 ring carbon atoms, phenyl, phenyl mono- or disubstituted by halogen, lower alkyl, lower alkoxy and/or trifluoromethyl, phenyl-lower alkyl or phenyl-lower alkyl mono- or disubstituted by halogen, lower alkyl, lower alkoxy and/or trifluoromethyl, another one of $R^1$, $R^2$ and $R^3$ is hydrogen or, in the case of $R^1$ and $R^2$, is hydroxy; and the remaining one of $R^1$, $R^2$ and $R^3$ is hydrogen, and to their salts, especially pharmaceutically acceptable salts, with the provisos given hereinbefore.

One embodiment of the invention consists of the sub-group A of compounds of formula I, wherein R has 2 or more carbon atoms and is lower alkyl, lower alkenyl, lower alkynyl, a cycloalkyl, hydroxycycloalkyl, cycloalkyl-loweralkyl, cycloalkyl-(hydroxy)lower alkyl or lower alkylthiocycloalkyl-(hydroxy)lower alkyl group having 3 to 6 ring carbon atoms, hydroxy-lower alkyl, hydroxy-lower alkenyl, mono-, di- or polyhalogeno-lower alkyl, mono-, di- or polyhalogeno-lower alkenyl, mono-, di-or polyhalogeno-(hydroxy)-lower alkyl, mono-, di- or polyhalogeno-(hydroxy)-lower alkenyl, phenyl-lower alkyl phenyl-lower alkyl mono- or disubstituted, in the phenyl moiety, by halogen, lower alkyl, lower alkoxy and/or trifluoromethyl or naphthyl-lower alkyl, and wherein one of the groups $R^1$, $R^2$ and $R^3$ represents hydrogen, lower alkyl, cycloalkyl, phenyl, phenyl substituted by halogen, lower alkyl, lower alkoxy and/or trifluoromethyl, phenyl lower alkyl or phenyl lower alkyl substituted in the phenyl moiety by halogen, lower alkyl, lower alkoxy and/or trifluoromethyl, another one of $R^1$, $R^2$ and $R^3$ is hydrogen or, in the case of $R^1$ and $R^2$ is hydroxy; and the remaining one of $R^1$, $R^2$ and $R^3$ is hydrogen, and their salts, especially pharmaceutically acceptable salts.

Compounds of subgroup A are, for example, these, wherein R has 2 or more carbon atoms and is, lower alkenyl or lower alkynyl, and wherein one of the groups $R^1$, $R^2$ and $R^3$ represents hydrogen, lower alkyl, cycloalkyl, phenyl, phenyl substituted by halogen, lower alkyl, lower alkoxy and/or trifluoromethyl, phenyl lower alkyl or phenyl lower alkyl substituted in the phenyl moiety by halogen, lower alkyl, lower alkoxy and/or trifluoromethyl, or one of $R^1$ and $R^2$ is hydroxy; and the remaining two of $R^1$, $R^2$ and $R^3$ are hydrogen, and their salts, especially pharmaceutically acceptable salts.

Another embodiment of the invention consists of the subgroup B of the compounds of formula I, wherein R is represented by lower alkoxy-lower alkyl, lower alkylthio-lower alkyl, lower alkanesulfinyl-lower alkyl, lower alkanesulfonyl-lower alkyl, di-lower alkoxy-lower alkyl, di-lower alkylthio-lower alkyl, lower alkoxy-(hydroxy)lower alkyl, lower alkoxy-(halogeno)-lower, oxa- or thiacycloalkyl having 2 to 6 ring carbon atoms, or dioxa- or dithiacycloalkyl having 3 to 5 ring carbon atoms, and wherein one of the groups $R^1$, $R^2$ and $R^3$ represents hydrogen, lower alkyl, cycloalkyl, phenyl, phenyl substituted by halogen, lower alkyl, lower alkoxy and/or trifluoromethyl, phenyl lower alkyl or phenyl lower alkyl substituted in the phenyl moiety by halogen, lower alkyl, lower alkoxy and/or trifluoromethyl, another one of $R^1$, $R^2$ and $R^3$ is hydrogen or, in the case of $R^1$ and $R^2$, is hydroxy; and the remaining one of $R^1$, $R^2$ and $R^3$ is hydrogen, provided that, if one of $R^1$ and $R^2$ is hydrogen, lower alkyl, cycloalkyl, phenyl, phenyl substituted by halogen, lower alkyl, lower alkoxy and/or trifluoromethyl, phenyl-lower alkyl or phenyl-lower alkyl substituted in the phenyl moiety by halogen, lower alkyl, lower alkoxy and/or trifluoromethyl, and the other two of $R^1$, $R^2$ and $R^3$ are hydrogen, R is different from 1,1-di($C_1$-$C_4$-alkoxy)-$C_1$-$C_5$-alkyl, and their salts, especially pharmaceutically acceptable salts, with the provisos given hereinbefore.

Compounds of subgroup B are, for example, those, wherein R is represented by lower alkoxy-lower alkyl, lower alkylthio-lower alkyl, di-lower alkoxy-lower alkyl, di-lower alkylthio lower alkyl, lower alkoxy-lower alkylthio-lower alkyl, oxacycloalkyl, thiacycloalkyl, dioxacycloalkyl and dithiacycloalkyl, and wherein one of the groups $R^1$, $R^2$ and $R^3$ represents hydrogen, lower alkyl, cycloalkyl, phenyl, phenyl substituted by halogen, lower alkyl, lower alkoxy and/or trifluoromethyl, phenyl lower alkyl or phenyl lower alkyl substituted in the phenyl moiety by halogen, lower alkyl, lower alkoxy and/or trifluoromethyl, or one of $R^1$ and $R^2$ is hydroxy; and the remaining two of $R^1$, $R^2$ and $R^3$ are hydrogen, and their salts, especially pharmaceutically acceptable salts, with the provisos given hereinbefore.

Preferred are compounds of formula I, wherein R has the meaning defined hereinbefore, and wherein one of the groups $R^1$, $R^2$ and $R^3$ represents hydrogen, lower alkyl, phenyl or phenyl substituted by halogen or lower alkyl, and the remaining two of $R^1$, $R^2$ and $R^3$ are hydrogen, and their salts, especially pharmaceutically acceptable salts.

Further preferred are compounds of formula I, wherein R is lower alkyl having 2 or more carbon atoms, lower alkenyl or lower alkynyl, $R^2$ represents hydrogen, lower alkyl, phenyl or phenyl substituted by halogen or lower alkyl and $R^1$ and $R^3$ are hydrogen, and pharmaceutically acceptable salts thereof.

Equally preferred is the subgroup B' of compounds of the formula I, wherein R is lower alkoxy-lower alkyl or mono- or dihydroxy-lower alkyl, $R^2$ represents hydrogen, lower alkyl, phenyl or phenyl substituted by halogen or lower alkyl and $R^1$ and $R^3$ are hydrogen, with the provisos given hereinbefore and pharmaceutically acceptable salts thereof.

The invention relates especially to compounds of the formula I, wherein R is $C_2$–$C_{12}$-alkyl, such as ethyl, butyl, isobutyl, pentyl or isopentyl, $C_2$–$C_7$-alkenyl, such as but-3-enyl, $C_2$–$C_7$-alkynyl, such as pent-3-ynyl, mono- or dihydroxy-$C_2$–$C_7$-alkyl, such as 2-(2-hydroxy)propyl, 2-(1,2-dihydroxy)propyl, 2-(2-hydroxy)butyl or 1-hydroxybutyl, mono-, di- or trihalogeno-$\alpha$-hydroxy-$C_3$–$C_7$-alkyl, such as 1-hydroxy-4,4,4-trifluoro-butyl, $\alpha$-saturated mono-, di- or trihalogeno-$\alpha$-hydroxy-$C_3$–$C_7$-alkenyl, such as 1-hydroxy-2-fluorobut-2-enyl, $C_1$–$C_4$-alkoxy-$C_1$–$C_4$-alkyl, such as 2-ethoxyethyl, di-$C_1$–$C_4$-alkoxy-$C_1$–$C_4$-alkyl, such as diethoxymethyl, $\alpha$-hydroxy-$C_3$–$C_6$-cycloalkyl, such as 1-hydroxycyclobutyl, $C_3$–$C_6$-cycloalkyl-$C_1$–$C_4$-alkyl, such as cyclopropylmethyl, $C_3$–$C_6$cycloalkyl-$\alpha$-hydroxy-$C_1$–$C_4$-alkyl, such as 1-cyclobutyl-1-hydroxymethyl, or 1-$C_1$–$C_4$-alkylthiocycloalkyl-$\alpha$-hydroxy-$C_1$–$C_4$-alkyl, (1-methylthiocyclopropyl)-(1-hydroxy)-methyl, $R^2$ represents hydrogen, hydroxy, $C_1$–$C_4$-alkyl, such as methyl, phenyl or phenyl substituted by halogen, such as chloro, or $C_1$–$C_4$ such as methyl and $R^1$ and $R^2$ are hydrogen or one of $R^1$ and $R^2$ denotes hydroxy and the other one as well as $R^3$ represents hydrogen, and to their salts, especially pharmaceutically acceptable salts, with the provisos given hereinbefore.

Even more preferred are subgroups A' and/or B' of compounds of formula I, wherein R either is $C_2$–$C_7$-alkyl, $C_2$–$C_7$-alkenyl or $C_2$–$C_7$-alkynyl or denotes $C_1$–$C_4$-alkoxy-$C_1$–$C_4$-alkyl or di-$C_1$–$C_4$-alkoxy-$C_1$–$C_4$-alkyl or denotes $\alpha$-, $\beta$-, $\gamma$- or $\delta$-hydroxy-$C_2$–$C_7$-alkyl or $\alpha,\beta$-dihydroxy-$C_2$–$C_7$-alkyl, $R^2$ represents hydrogen, lower alkyl, phenyl or phenyl substituted by halogen or lower alkyl, and $R^1$ and $R^3$ are hydrogen, with the provisos given hereinbefore, and pharmaceutically acceptable salts thereof, with the provisos given hereinbefore.

Especially preferred are compounds of the formula I, wherein R denotes $C_2$–$C_7$-alkyl, such as ethyl, butyl, isobutyl, pentyl or isopentyl, $\alpha$-saturated $C_3$–$C_7$-alkenyl, such as but-3-enyl, $\alpha$-saturated $C_3$–$C_7$-alkynyl, such as pent-3-ynyl, $\alpha$-, $\beta$-, $\gamma$- or $\delta$-hydroxy-$C_2$–$C_7$-alkyl, such as 2-(2-hydroxy)propyl or 1-hydroxybutyl, $\alpha,\beta$-dihydroxy-$C_2$–$C_4$-alkyl, such as 2-(1,2-dihydroxy)propyl, mono-, di- or trifluoro-$\alpha$-hydroxy-$C_3$–$C_7$-alkyl, such as 1-hydroxy-4,4,4-trifluorobutyl, $\alpha$-saturated mono-, di- or trihalogeno-$\alpha$-hydroxy-$C_3$–$C_7$-alkenyl, such as 1-hydroxy-2-fluorobut-2-enyl, $C_1$–$C_4$-alkoxy-$C_1$–$C_4$-alkyl, such as 2-ethoxyethyl, di-$C_1$–$C_4$-alkoxy-$C_1$–$C_4$-alkyl, $C_3$–$C_6$-cycloalkyl-$C_1$–$C_4$-alkyl, such as cyclopropylmethyl, $\alpha$-hydroxy-$C_3$–$C_6$-cycloalkyl, such as 1-hydroxycyclobutyl, or $C_3$–$C_6$-cycloalkyl-$\alpha$-hydroxy-$C_1$–$C_4$-alkyl, such as 1-cyclopropyl-1-hydroxymethyl, and $R^1$, $R^2$ and $R^3$ represent hydrogen, and to their salts, especially pharmaceutically acceptable salts.

Very especially preferred are subgroups A and/or B of compounds of formula I, wherein R is $C_2$–$C_7$-alkyl, $C_2$–$C_7$-alkenyl or $C_2$–$C_7$-alkynyl, or $C_1$–$C_4$-alkoxy-$C_1$–$C_4$-alkyl or di-$C_1$–$C_4$-alkoxy-$C_1$–$C_4$-alkyl and $R^1$, $R^2$ and $R^3$ are hydrogen, and pharmaceutically acceptable salts thereof, with the provisos given hereinbefore.

Most preferred is subgroup(s) A and/or B compounds of formula I, wherein R is $C_3$–$C_7$-alkyl and $R^1$, $R^2$ and $R^3$ are hydrogen, and pharmaceutically acceptable salts thereof.

The invention specifically relates to compounds of the formula I described in the Examples herein, and to their salts, especially pharmaceutically acceptable salts.

Although salts of compounds of the formula I are included in the above definitions of preferred compounds, the invention predominantly relates to the free compounds of formula I.

The process for the manufacture of compounds of the formula I, is characterized in that a) in a compound of formula II

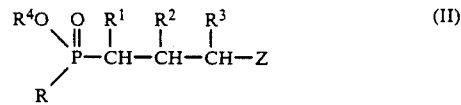

in which R, $R^1$, $R^2$ and $R^3$ have their previous significances, Z represents —$NH_2$ and $R^4$ denotes a hydroxy-protective group $R^5$ or, when $R^1$ and $R^3$ denote hydrogen and $R^2$ denotes hydrogen or alkyl, denotes an alkali metal or ammonium ion $R^6$, or Z represents a protected or latent amino group $Z^o$ and $R^4$ denotes hydrogen or a hydroxy-protective group $R^5$, any group $R^5$ or $R^6$ is replaced by hydrogen and/or any group $Z^o$ is converted into —$NH_2$; or b) in a compound of the formula III

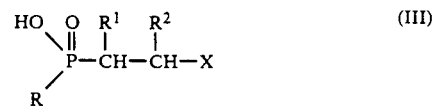

in which R, $R^1$ and $R^2$ have their previous significances and X is a group capable of being converted into a group of formula —$CH(R^3)NH_2$, the group X is converted into a group of formula

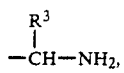

wherein $R^3$ has its previous significance; or c) a compound of formula I', said compound of formula I' being otherwise identical to a compound of formula I but having one or more carbon-carbon-multiple bond(s) is reduced to produce a compound of formula I, and, if desired, a resulting salt obtained in this process may be converted into the free compound or into another salt and/or, if desired, a resulting free compound is converted into a salt to suit the above definition and/or, if desired, a resulting mixture of isomers is separated into the individual isomers.

Protected hydroxy groups such as groups $-OR^5$ present in a protected form in starting materials of the formula II are, for example, etherified hydroxy groups, such as hydroxy groups etherified with aliphatic, cycloaliphatic or araliphatic alcohol, e.g. with a lower alkanol, a cycloalkanol, or a phenyl- or diphenyl-lower alkanol, or hydroxy groups etherified with an aliphatic silanol, e.g. with a tri-lower alkyl silanol. As groups $R^5O-$, lower alkoxy, e.g. $C_1-C_4$-alkoxy, mono- or diphenyl-lower alkoxy, e.g. 1-phenyl- or 1,1-diphenyl-$C_1-C_4$-alkoxy, and tri-lower alkylsilyloxy, e.g. tri-$C_1-C_4$-alkyl-, such as trimethylsilyloxy, are especially preferred.

Protected amino groups $Z^o$ in starting materials of the formula II are, for example, acylamino groups such as lower alkanoylamino, e.g. acetylamino, or phthalimido, lower alkoxycarbonylamino unsubstituted or substituted by phenyl, e.g. benzyloxycarbonylamino or tert-butoxycarbonylamino groups, or 1-aryl-methylamino groups e.g. benzylamino, or 1-phenyl-lower alkylamino, silylated amino groups, such as tri-lower alkylsilylamino or especially bis-(tri-lower alkylsilyl)amino, e.g. bis trimethyl silylamino. A latent amino group $Z^o$ may be e.g. nitro or azido.

Preferred compounds of formula II are those having the formula IIa

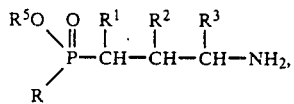

wherein $R^5$ represents a hydroxy-protective group, for example, $C_1-C_4$-alkyl or $C_1-C_4$-alkyl substituted by lower alkanoyloxy or by one or two optionally substituted phenyl groups, such as 1-$C_2-C_7$-alkanoyloxy-$C_1-C_4$-alkyl, e.g. pivaloyloxymethyl, or 1-phenyl- or 1,1-diphenyl-$C_1-C_4$-alkyl, e.g. benzyl, or having the formula IIb

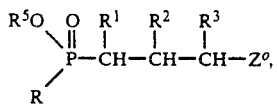

wherein $R^5$ represents a hydroxy-protective group, for example, $C_1-C_4$-alkyl, $C_1-C_4$-alkyl substituted by one or two optionally substituted phenyl groups, such as 1-phenyl- or 1,1-diphenyl-$C_1-C_4$-alkyl, e.g. benzyl, or a silyl group, such as tri-$C_1-C_4$-alkylsilyl, e.g. trimethylsilyl, and $Z^o$ has its previous significance and denotes, for example, $C_1-C_7$-alkanoylamino, e.g. acetylamido, phthalimido or bis-silylamino, such as bis(tri-$C_1-C_4$-alkylsilyl)amino, e.g. bis(trimethylsilyl)amino, or having the formula IIc

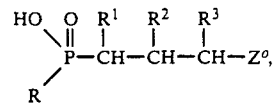

wherein $Z^o$ has its previous significance and denotes, for example, $C_1-C_7$-alkanoylamino, e.g. acetylamino, $C_1-C_4$-alkoxycarbonylamino, e.g. tert.-butyloxycarbonylamino, or phenyl-$C_1-C_4$-alkoxycarbonylamino, or having the formula

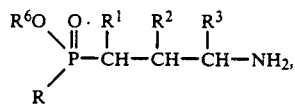

wherein $R^6$ denotes an alkalimetal or ammonium ion, and wherein in formulae IIa, IIb and IIc R, $R^1$, $R^2$ and $R^3$ have their previous significance or in formula IId R denotes an unsubstituted aliphatic, cycloaliphatic or araliphatic hydrocarbon residue, $R^1$ and $R^3$ represent hydrogen and $R^2$ denotes hydrogen or alkyl.

The replacement of the protective group $R^5$ in compounds of formula II, IIa or IIb by hydrogen may be effected by treatment with a suitable nucleophilic reagent such as an alkali metal hydroxide, e.g. sodium hydroxide, or lithium hydroxide, an alkali metal halide, particularly bromide or iodide such as lithium bromide or sodium iodide, thiourea, an alkali metal thiophenolate such as sodium thiophenolate. The replacement reaction may be carried out in the absence or presence of a solvent and, if necessary, while cooling or heating, in a closed vessel and/or under an atmosphere of an inert gas.

When $R^5$ denotes $C_1-C_4$-alkyl substituted in 1-position by one or two phenyl groups, e.g. when $R^5$ is benzyl, the replacement of such a group in compounds of formulae II, IIa or IIb by hydrogen may be effected by hydrogenolysis in the presence of a metallic hydrogenation catalyst, or any other suitable procedure.

Alternatively, the replacement of the protective group, e.g. of a silyl or alkyl group, $R^5$ in compounds of formulae II, IIa or IIb or of an alkalimetal or ammonium ion $R_6$ in compounds of the formulae II or IId by hydrogen may be effected by treatment with an acid under hydrolytic conditions, especially with a mineral acid such as a hydrohalic acid e.g. hydrochloric acid which is used in dilute or concentrated aqueous form, or by treatment with an organic silyl halide such as trimethylsilyl iodide or bromide, followed by hydrolysis, if necessary. The reaction is preferably conducted at elevated temperature e.g. while refluxing the reaction mixture and, if necessary using an organic diluent, in a closed vessel and/or under an atmosphere of an inert gas. The kind of replacement of the protective group $R^5$ depends e.g. on the substituent R present in a compound of formula II which must be retained in converting a compound of formula II to a compound of formula I. Said replacement may be effected e.g. according to the illustrating examples.

Protected amino group or latent amino groups $Z^o$ in compounds of formula II, IIb or IIc may be converted into free amino according to known methods, which are selected according to the characteristics of the protected or latent amino group to be converted into amino, such as solvolytic or hydrogenolytic procedures, for example, hydrolysis in the presence of an acid or a base, acidolysis, e.g. treatment with trifluoroacetic acid, treatment with hydrazine, or hydrogenolysis in the presence of a metallic hydrogenation catalyst, or any other suitable procedure.

Depending on the groups involved, the replacement and conversion operations may be carried out in any sequence or simultaneously by methods which are well known per se.

It is preferred that all protecting groups are converted, $R^5$ or $R^6$ being converted to H and $Z^o$ being converted to $NH_2$, in a single step, by treatment with an acid, preferably a hydrohalic acid, especially hydrochloric acid, under hydrolytic conditions.

The compounds of formula II may be prepared, for example, by various methods according to the nature of the group X in the formula V defined hereinafter, e.g. by reacting, in the presence of a basic catalyst or in the presence of agents forming free radicals, a compound of the formula IV

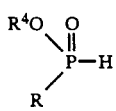
(IV)

in which R and $R^4$ have their previous significance which can be prepared by reaction of a compound of the formula R-PHal$_2$ (IVa; Hal=halogen) with an alcohol $R^5OH$ in the presence of a tri-lower alkylamine or, more advantageously, by reaction of aqueous hypophosphorous acid with an orthoester of the formula $C(C_1-C_4-alkyl)(OR^5)_3$ (IVb) yielding, in the latter case, a compound IV, wherein R denotes $C(C_1-C_4-alkyl)-(OR^5)_2$, with a compound of formula V

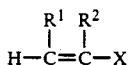
(V)

in which $R^1$ and $R^2$ have their previous significance and X is a group capable of being converted into a group of formula —CH($R^3$)—Z, wherein $R^3$ and Z have their previous significances, in order to produce a compound of formula VI

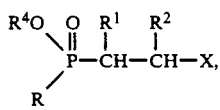
(VI)

wherein $R^1$, $R^2$, $R^4$, R and X have their previous significances; and then converting the group X into a group of formula —CH($R^3$)—Z.

A group X is primarily cyano but may also represent carbamoyl, a group of formula —CH($R^3$)—$Z^o$ (VIa) in which $R^3$ and $Z^o$ have their previous significance; or X is a group of formula —C($R^3$)=Y in which $R^3$ has its previous significance and —C=Y is an optionally functionally modified carbonyl group such as a corresponding ketal or thioketal group, including a corresponding cyclic group.

When, in a compound of formula IV $R^4$ has its previous significance and, in the compound of formula V, X is an activating group Xa such as cyano or —C($R^3$)=O, then either a basic catalyst or a free radical catalyst may be employed. When, however, the same compounds of formula IV are reacted with compounds of formula V in which X is e.g. a residue of formula—CH($R^3$)—$Z^o$, then free radical catalysts are required.

A basic catalyst used in the first step may be e.g. an alkali metal $C_1$-$C_4$-alkoxide, for example, a sodium or potassium $C_1$-$C_4$-alkoxide, in particular sodium methoxide, sodium ethoxide or potassium tert-butoxide, an alkaline or alkaline earth metal fluoride, such as potassium fluoride or caesium fluoride, or an alkali metal hydride, such as sodium hydride. The reaction may be effected with or without the use of an added solvent. If a solvent is added, this is preferably an alcohol, in particular a $C_1$-$C_4$-alkanol corresponding to the alkoxide used as basic catalyst. The reaction temperature may vary from 0° C. to the boiling point of any added solvent.

Agents forming free radicals are, for example, compound convertible into free radicals by ionizing or ultra-violet radiation, preferably peroxy compounds, such as inorganic peroxy compounds, e.g. hydrogen peroxide or ammonium persulfate, or organic peroxides, e.g. benzoyl peroxide or tert-butyl peroxide, or organic azo compounds, e.g. azo-bis-isobutyronitrile. Reactions involving free radical-forming agents may be conducted in the optional presence of a solvent and, if necessary, while cooling or heating, in a closed vessel and/or in an atmosphere of an inert gas.

The conversion of a group X into the group —CH($R^3$)—Z is carried out according to known methods. Cyano and carbamoyl are converted into aminomethyl by reduction, cyano, for example, by hydrogenation in the presence of a suitable catalyst, e.g. Raney nickel and of a solvent, such as ethanol, which may preferably contain ammonia, and carbamoyl, for example, by treatment with a suitable hydride reducing agent, such as borane in tetrahydrofuran.

The conversion of a group X in the compounds of formula VI in which X is a group —C($R^3$)=Y, in which Y is oxygen, into the group of the formula —CH($R^3$)—Z is carried out by known reductive amination procedures, e.g. treatment with sodium cyanoborohydride in the presence of ammonium acetate in a suitable solvent, such as dioxane, and while cooling, e.g. at about 0° C.

The compounds of formula IV are either known or they may be prepared by methods as described hereinbefore. Specific examples of compounds of formula IV include: iso-propyl (ethyl)phosphonite, isopropyl (n-propyl)phosphonite, iso-butyl (n-butyl)phosphonite, iso-butyl (iso-propyl)phosphonite, iso-butyl (iso-butyl)-phosphonite and iso-butyl (sec.-butyl)-phosphonite.

Likewise, compounds of formula V are either known or can be obtained by methods which are well known.

Alternatively, a compound of the formula VII

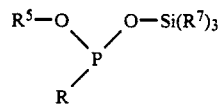
(VII)

in which $R^5$ is $C_1$-$C_4$-alkyl or $C_1$-$C_4$-alkyl substituted by one or two phenyl residues or an additional group —Si($R^7$)$_3$, each $R^7$, independently, is $C_1$-$C_6$-alkyl, preferably $C_1$-$C_2$-alkyl, particularly methyl, the groups $R^5$ and $R^7$ being the same or different, can be reacted with a compound of the formulae

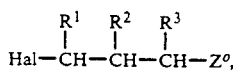 (VIIIa)

 (VIIIb)

 (VIIIc)

or

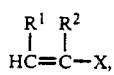 (V)

in which $R^1$, $R^2$, $R^3$, $Z^o$ and X have their previous significances, X being primarily cyano or a group of the formula $-C(R^3)=Y$ and Hal stands for halogen, such as iodo, bromo or chloro. The reaction with an epoxide of formula VIIIb is advantageously carried out in the presence of a mild Lewis acid, such as anhydrous zinc chloride, whilst the reactions with halides of formulae VIIIa or VIIIc are preferably carried out under the conditions of the Arbusov method, e.g. at a reaction temperature ranging from room temperature to an elevated temperature, e.g. 160° C., while removing the trialkyl silyl halide formed in the reaction.

The compounds of formula IIb and/or IIc may also be prepared starting from and reacting, e.g. acylating a compound of formula IX

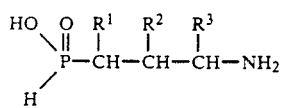 (IX)

wherein $R^1$, $R^2$ and $R^3$ have their previous significances to give a compound of formula X

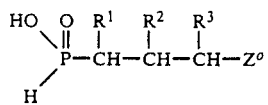 (X)

wherein $R^1$, $R^2$ and $R^3$ have their previous significance and $Z^o$ is an e.g. acylated amino group and, subsequently, protecting the (acid) hydroxyl group in the compound of formula X to produce a compound of formula XI

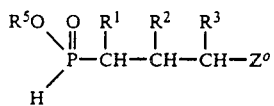 (XI)

wherein $R^1$, $R^2$, $R^3$ and $Z^o$ have their previous significances and $R^5O$ denotes protected, e.g. esterified, hydroxy. Alternatively, the starting material of formula IX can be reacted with a silylating agent, such as a hexa-lower alkyl silazane or a tri-lower alkyl halogenosilane, e.g. with hexamethyldisilazane, or with trimethylchlorsilane in the presence of triethylamine, to produce a compound of formula

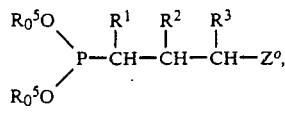 (XI')

wherein $R^5O$ a group $R^5$ being denotes tri-lower alkylsilyl, e.g. trimethylsilyl, and $Z^o$ denotes bis(tri-lower alkylsilyl)amino, such as bis(trimethylsilylamino).

The intermediate of the formula XI or XI' is then reacted with a compound capable of converting the

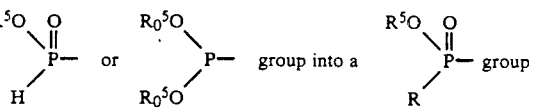

wherein R has its previous significance to produce a compound of formula IIb, in which $R^5$ has its previous significance. Thus, the intermediate of the formula XI may be reacted, in the presence of a basic condensation agent, such as a tri-lower alkyl amine, e.g. of N-ethyl-N,N-diisopropyl-amine, with a corresponding halide, e.g. a lower alkyl halide of the formula R-Hal (XIIc, Hal=halogen), preferably under basic conditions, or may be reacted, for the manufacture of compounds IIb, in which R is an aliphatic, cycloaliphatic-aliphatic or araliphatic radical having at least 2 carbon atoms in each of the aliphatic moieties, in which radical R the carbon atom via which R is bonded to the P-atom is unsubstituted and the adjacent carbon atom is not substituted by hydroxy or, in the case of aliphatic radicals R, by halogen or, in the case of cycloaliphatic-aliphatic radicals R, by lower alkylthio, with a terminally unsaturated aliphatic, cycloaliphatic-aliphatic or araliphatic compound R'''-H (XIIb), wherein R''' is a group otherwise identical to the radical R in the desired end product IIb but has one additional terminal double bond between the carbon atom via which R is bonded to the P-atom and the adjacent carbon atom, or may be reacted, for the manufacture of compounds IIb, in which the carbon atom via which R is bonded to the P-atom is substituted by one hydroxy group, with an aliphatic, cycloaliphatic, cycloaliphatic-aliphatic or araliphatic aldehyde or ketone (XIIa), which compound XIIa corresponds, if the aldehyde or ketone functional group is replaced by one free valence and one hydroxy group, to the group R in the desired end product IIb.

The starting materials of formula IX and their production have been described in U.S. Pat. No. 4656298 which discloses the replacement, in a compound of formula XIII'

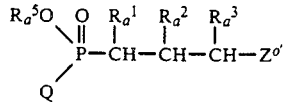 (XIII')

wherein one of $R_a^1$, $R_a^2$ and $R_a^3$ is hydrogen, $C_1$-$C_8$-alkyl, $C_3$-$C_6$-cycloalkyl, phenyl optionally substituted by halogeno, $C_1$-$C_4$-alkyl, $C_1$-$C_4$-alkoxy and/or $CF_3$, or is $C_7$-$C_{10}$-phenylalkyl optionally substituted in the phenyl moiety by halogeno, $C_1$-$C_4$-alkyl, $C_1$-$C_4$-alkoxy and/or $CF_3$, and the other two are hydrogen, $Z^{o'}$ is a protected amino group, $R_a^5$ is hydrogen, $C_1$-$C_4$-alkyl or an alkali metal or ammonium cation and Q is hydrogen or a protecting group, replacing to group $R_a{}^5$, when it is alkyl, by hydrogen or by an alkali metal or ammonium cation;

replacing the group Q when it is a protecting group, by hydrogen; and converting $Z_a{}^o$ into $NH_2$, to produce a compound of formula IX.

In U.S. Pat. No. 4656298, protecting groups Q e.g. —C($C_1$-$C_4$-alkyl)($OR^a$)($OR^b$), preferably —CH($OR^a$)-($OR^b$) in which $R^a$ and $R^b$ are $C_1$-$C_4$-alkyl, especially —CH($OC_2H_5$)$_2$ and/or a $C_1$-$C_4$-alkyl group $R_a{}^5$, may be replaced by hydrogen by treating the compound of formula XIII' with an acid under hydrolytic conditions; or by treatment with an organic silyl halide such as trimethyl silyl iodide or bromide, followed by hydrolysis. It is preferred in U.S. Pat. No. 2656298, to replace protecting groups Q and $R_a{}^5$ by hydrogen, and convert $Z_a{}^o$ into $NH_2$ in compounds of formula XIII', in a single step, with an acid under hydrolytic conditions.

This known method has the disadvantage that, under the drastic reacting conditions disclosed, the hydroxy-protecting group $R_a{}^5$ and the amino-protecting group are removed simultaneously with the protecting group Q.

It has now been found that in a compound of formula XIII or XIV $$\begin{array}{c} R^5O \quad O \quad R^1 \quad R^2 \quad R^3 \\ \diagdown \| \quad | \quad | \quad | \\ P-CH-CH-CH-Z^o \\ \diagup \\ Q \end{array} \quad (XIII)$$

or $$\begin{array}{c} R^5O \quad O \quad R^1 \quad R^2 \\ \diagdown \| \quad | \quad | \\ P-CH-CH-X, \\ \diagup \\ Q \end{array} \quad (XIV)$$

wherein $R^1$, $R^2$, $R^3$, $R^5$, Q, X and $Z^o$ have their previous significance, the respective protecting groups $R^5$ and $Z^o$, or $R^5$ and X, respectively, are retained, when the compound of formula XIII or XIV is treated with a protic anhydrous medium, to produce a compound of formula XI, or a compound of formula $$\begin{array}{c} R^5O \quad O \quad R^1 \quad R^2 \\ \diagdown \| \quad | \quad | \\ P-CH-CH-X. \\ \diagup \\ H \end{array} \quad (XV)$$

Examples of such protic anhydrous media include:

anhydrous hydrogen chloride gas, or an anhydrous medium may be generated from an organic compound having one or more Si—Cl bonds together with an agent e.g. an alkanol capable of cleaving the Si—Cl bond, to produce an anhydrous protic medium in situ.

Preferred anhydrous protic media include therefore trimethyl silyl chloride in technical chloroform which contains ethanol.

This novel route has the advantage that re-protecting steps, e.g. IX→X and X→XI, necessary for known routes, are avoided.

The invention, therefore, also relates to a process for the manufacture of compounds of the formula $$\begin{array}{c} R_b{}^5O \quad O \quad R^1 \quad R^2 \\ \diagdown \| \quad | \quad | \\ P-CH-CH-X, \\ \diagup \\ H \end{array} \quad (XV)$$

wherein X denotes cyano, carbamoyl or a group of the formulae —CH($R^3$)-$Z^o$ (XVa) or —C($R^3$)=Y (XVb) in which $Z^o$ denotes a protected or latent amino group as specified hereinbefore, Y denotes an optionally acetalised, thioacetalised, ketalised or thioketalised oxo group, one of $R^1$, $R^2$ and $R^3$ is hydrogen, hydroxy, $C_1$-$C_8$-alkyl, $C_3$-$C_6$-cycloalkyl, phenyl optionally substituted by halogen, $C_1$-$C_4$-alkyl, $C_1$-$C_4$-alkoxy and/or trifluoromethyl or is $C_7$-$C_{10}$-phenylalkyl optionally substituted in the phenyl moiety by halogen, $C_1$-$C_4$-alkyl, $C_1$-$C_4$-alkoxy and/or trifluoromethyl and the others of $R^1$, $R^2$ and $R^3$ are hydrogen, and $R_b{}^5$ denotes a $C_1$-$C_4$-alkyl radical, characterised in that a compound of the formula $$\begin{array}{c} R_b{}^5O \quad O \quad R^1 \quad R^2 \\ \diagdown \| \quad | \quad | \\ P-CH-CH-X, \\ \diagup \\ Q' \end{array} \quad (XIV)$$

wherein $R^1$, $R^2$, $R^3$, $R_b{}^5$ and X have the meanings given hereinbefore and Q' denotes a group of the formula —C($R^8$)—C($OR^9$)($OR^{10}$) (XIVa) in which $R^8$ denotes lower alkyl and $R^9$ and $R^{10}$, independently of one another, represent lower alkyl or together represent lower alkylene, is treated with an anhydrous protic medium, and to compounds of formula XV, whenever manufactured by this process or an obvious chemical equivalent thereof.

The novel process is carried out at a temperature ranging from −80° C. to 100° C., preferably from 0° C.-50° C.

While the relative molar ratios of the reactants i.e. of reactant XIV to the organic silyl chloride, used may vary within a wide range, it is preferred to use molar ratios ranging from 1 to 2 molar equivalents of the latter, per molar equivalent of XIV.

In a preferred embodiment of process variant a) for the manufacture of compounds of formula I a compound of the formula IIa $$\begin{array}{c} R^5O \quad O \quad R^1 \quad R^2 \quad R^3 \\ \diagdown \| \quad | \quad | \quad | \\ P-CH-CH-CH-NH_2, \\ \diagup \\ R \end{array} \quad (IIa)$$

wherein $R^5$ denotes lower alkyl and R, $R^1$, $R^2$ and $R^3$ have their previous significances which may be obtained, for example, according to the reaction sequences IV+V→VI→IIa;
VII+VIIIc→
VI→IIa;
VII+VIIIb→(IIb)→IIa or
XIV→XV→VI→IIa;

is subjected to basic or acidic hydrolysis or is treated with a tri-lower alkyl halogenosilane.

The combined process characterised by the reaction sequence

XIV→XV→VI→IIa→I is a novel and advantageous route to compounds of formula I.

The invention, therefore also relates to a process for the manufacture of compounds of the formula I

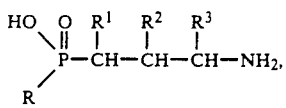

wherein R denotes an aliphatic, cycloaliphatic, cycloaliphatic-aliphatic or araliphatic radical having 2 or more carbon atoms, and wherein one of the groups $R^1$, $R^2$ and $R^3$ represents hydrogen or an aliphatic, cycloaliphatic, araliphatic or aromatic radical, another one of $R^1$, $R^2$ and $R^3$ is hydrogen, or in the case of $R^1$ and $R^2$, is hydroxy, and the remaining one of $R^1$, $R^2$ and $R^3$ is hydrogen, and to their salts, characterised in that a compound of the formula

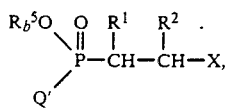

wherein $R_b^5$ denotes a $C_1$-$C_4$-alkyl radical, X denotes cyano, carbamoyl or a group of the formulae —CH($R^3$)—$Z^o$ (XVa) or —C($R^3$)=Y (XVb) in which $Z^o$ denotes a protected or latent amino group as specified hereinbefore, Y denotes an optionally acetalised, thioacetalised, ketalised or thioketalised oxo group and Q' denotes a group of the formula —C($R^8$)-(O$R^9$)(O$R^{10}$) (XIVa) in which $R^8$ denotes lower alkyl and $R^9$ and $R^{10}$, independently of one another, represent lower alkyl or together represent lower alkylene and $R^1$, $R^2$ and $R^3$ have the meanings given hereinbefore, is treated with an anhydrous protic medium, the resulting compound of the formula

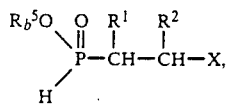

wherein $R^1$, $R^2$, $R_b^5$ and X have their previous significances is reacted with an aldehyde or ketone XIIa or with a compound of the formulae R'''-H (XIIb) or R-Hal (XIIc) wherein Hal R and R''' and the compound XIIa have their previous significances, in the resulting compound of formula VI

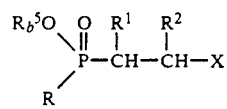

wherein $R^1$, $R^2$, $R_b^5$, R and X have their previous significances; the group X is converted into a group of formula —CH($R^3$)—NH$_2$ (IIa') and the resulting compound of formula IIa

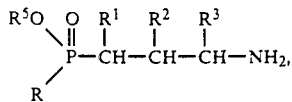

wherein R, $R^1$, $R^2$, $R^3$ and $R_b^5$ have their previous significances is converted into the corresponding compound of formula I.

In this context, X is preferably cyano, the anhydrous protic medium is preferably generated from trimethylsilychloride and commercial-grade chloroform, the intermediate XV is preferably reacted with a compound XIIc and/or the conversion of the cyano group into the —CH$_2$NH$_2$ group is preferably effected by hydrogenolysis.

In another preferred embodiment of process variant a), a compound of the formula IIc

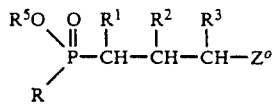

wherein R, $R^1$, $R^2$, $R^3$, $R^5$ and $Z^o$ have their previous significances, which may be prepared, for example, via the reaction sequences IX→X→XI→IIb or
IX→XI'→IIb, is subjected to basic or acidic hydrolysis or is treated with a tri-lower alkyl halogenosilane followed by aqueous workup. Advantageously, a compound IIb, wherein $R^5$ denotes tri-lower alkylsilyl, $Z^o$ denotes bis(lower alkylsilyl)amino and $R^1$, $R^2$ and $R^3$ have their previous significances, is formed in situ by reacting a compound of the formula

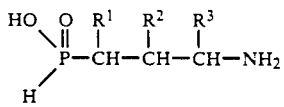

with a silylating agent and subsequently, preferably under basic conditions, with a compound of the formula R-Hal (XIIb; Hal=halogen) and de-protected according to the invention, when worked up under protic, e.g. aqueous or aqueous/alcoholic conditions.

The conversion of the group X into a group of formula —CH($R^3$)—NH$_2$ according to process variant b) may be effected by any of the methods described hereinbefore, e.g. by a variation of the conversion of compounds of formula VI into compounds of formula II.

The reaction is carried out according to known methods, in the absence or presence of a solvent, which may also serve as a reagent, if necessary, while cooling or heating, in a closed vessel and/or in the atmosphere of an inert gas.

The starting materials of the formula III may be prepared, for example, from compounds of the formula VI by converting the group $R^5O$- into hydroxy, the reaction being carried out according to the previously described procedure, e.g. by acidic hydrolysis, such as by treatment with an aqueous mineral acid, e.g. hydrochloric acid, or by treatment with a nucleophilic reagent.

In process variant c), a compound of formula I' may have its unsaturation within the substituent R such that it is e.g. of the formula I''

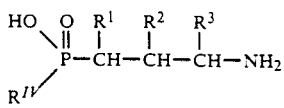

In this case $R^{IV}$ may be selected from lower alkenyl, lower alkanedienyl or lower alkynyl, to produce a compound of formula I, wherein R is lower alkyl, or phenyl to produce a compound of formula I wherein R is cyclohexyl.

The reduction may be effected by any suitable reducing agent, such as hydrogen in the presence of a catalyst, for the reduction of aryl e.g. Nishimura catalyst and for the reduction of aliphatic multiple bonds e.g. Palladium on charcoal, in the presence or absence of a solvent and at room temperature or elevated temperature.

The compounds of formula I' may be produced according to any of the methods described herein for the manufacture of compounds of formula I starting from starting materials having the respective unsaturated substituents. Furthermore, compounds of formula I" may also be obtained starting from the corresponding $R^{IV}$-dichlorophosphine by reaction with lower alkanol, such as ethanol, and a tri-lower alkylamine, such as triethylamine, reacting the resulting $R^{IV}$-phosphonous acid ester with a compound of formula $HC(R^1)=C(R^2)-X$ (V; X=e.g. CN) and converting the group X into the corresponding group $-CH(R^3)-NH_2$.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures preferably near the boiling point of the solvents used, at atmospheric or superatmospheric pressure.

Compounds of the formula I obtainable according to the process of the invention may be interconverted into another.

Thus, compounds of formula I, wherein R is substituted by hydroxy, and/or $R^1$ or $R^2$ denotes hydroxy, can be converted into the corresponding hydroxy-free compounds, for example, by reacting with thiocarbonyldiimidazole and treating the resulting imidazolylthiourethane in the presence of a radical-initiator, such as azoisobutyronitrile, with a tri-lower alkylstannane, e.g. with $(C_4H_9)_3SnH$, for example in benzene at 60° to 80° C.

Also double and/or triple bonds present in the group R may be reduced to single bonds, triple bonds also to double bonds to yield the corresponding less unsaturated compound of formula I.

The invention further includes any variant of the present processes, in which an intermediate product obtainable at any stage thereof is used as starting material and the remaining steps are carried out, or in which the starting materials are formed under the reaction conditions, or in which the reaction components are used in the form of their salts or optically pure antipodes. Whenever desirable, the above processes are carried out after first suitably protecting any potentially interfering reactive functional groups, e.g. as illustrated herein.

Advantageously, those starting materials should be used in said reactions that lead to the formation of those compounds indicated above as being preferred.

The invention also relates to novel starting materials and processes for their manufacture. Thus, compounds of formula IIa and IIc except those, wherein $R^1$ and $R^3$ denote hydrogen, $R^2$ is hydrogen or alkyl and R denotes an unsubstituted aliphatic cycloaliphatic or araliphatic radical, or one of $R^1$, $R^2$ and $R^3$ represents hydrogen or an aliphatic, cycloaliphatic, araliphatic or aromatic radical and the other two of $R^1$, $R^2$ and $R^3$ denote hydrogen and R is $-CH(O-C_1-C_4 \text{alkyl})_2$ or $-C(C_1-C_4 \text{alkyl})(O-C_1-C_4 \text{alkyl})_2$ and compounds of formula IIb except those in which one of $R^1$, $R^2$ and $R^3$ represents hydrogen or an aliphatic, cycloaliphatic, araliphatic or aromatic radical and the other two of $R^1$, $R^2$ and $R^3$ denote hydrogen and R is $-CH(O-C_1-C_4 \text{alkyl})_2$ or $-C(_1-C_4 \text{alkyl})(O-C_1-C_4 \text{alkyl})_2$, are new. Those new compounds form further aspects of the invention.

Depending on the choice of starting materials and methods, the new compounds may be in the form of one of the possible isomers, for example, as diastereomers, as optical isomers (antipodes), as racemates, or as mixtures thereof.

In case diastereomeric mixtures of the above compounds or intermediates are obtained, these can be separated into the single racemic or optically active isomers by methods in themselves known, e.g. by fractional distillation, crystallization or chromatography.

The racemic products of formula I or basic intermediates can be resolved into the optical antipodes, for example, by separation of diastereomeric salts thereof, e.g., by the fractional crystallization of d- or l-(tartrate, dibenzoyltartrate, mandelate or camphorsulfonate) salts.

Advantageously, the more active of the antipodes of the compounds of this invention is isolated.

Furthermore, the compounds of the invention are either obtained in the free (Zwitterion-) form, or as a salt thereof. For example, any resulting free compound can be converted into a corresponding acid addition salt, preferably with the use of a pharmaceutically acceptable acid or anion exchange preparation, salts with bases by treatment of the free compounds with bases or suitable cation exchange techniques, or resulting salts can be converted into the corresponding free compounds, for example the acid addition salts, with the use of a stronger base, such as a metal or ammonium hydroxide, or any basic salt, e.g., an alkali metal hydroxide or carbonate, or a cation exchange preparation and the salts with bases by treatment with suitable acidic reagents. These or other salts, for example, the picrates, can also be used for purification of the compounds obtained; the compounds are then first converted into salts. In view of the close relationship between the free compounds and the compounds in the form of their salts, whenever a compound is referred to in this context, a corresponding salt is also intended, provided such is possible or appropriate under the circumstances and the term "salts" shall, if desired also include the free compounds, where appropriate according to meaning and purpose.

The compounds, including their salts, may also be obtained in the form of their hydrates, or include other solvents used for the crystallization.

The present invention also relates to the use of the compounds of the invention for the preparation of pharmaceutical compositions, especially pharmaceutical compositions having selective $GABA_B$-antagonistic activity which can be used for the treatment of e.g. cognitive and memory disorders, depressive states of mind and anxieties.

The pharmaceutical compositions according to the invention are those suitable for enteral, such as oral or rectal, transdermal and parenteral administration to mammals, including man, for the treatment of diseases responsive to $GABA_B$-receptor blocking as given above, comprising an effective $GABA_B$-receptor blocking amount of a compound of the invention, alone or in combination with one or more pharmaceutically acceptable carriers.

The pharmacologically active compounds of the invention are incorporated into pharmaceutical compositions comprising an effective amount thereof in conjunction or admixture with excipients or carriers suitable for either enteral or parenteral application.

Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salts and/or polyethylene glycol; for tablets also c) binders, e.g. magnesium aluminum silicate, starch paste, gelatin, tragacanth, methylcellulose, sodium carboxymethylcellulose and/or polyvinylpyrrolidone; if desired, d) disintegrants, e.g. starches, agar, alginic acid or its sodium salt, or effervescent mixtures; and/or e) absorbents, colourants, flavours and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

The present invention also relates to the use of compounds of the invention having $GABA_B$-antagonistic properties and pharmaceutical compositions comprising said compounds for the treatment in mammals of disorders responsive to selective $GABA_B$-receptor blocking, particularly cognitive and memory disorders, and also of depressions and anxieties.

One aspect relates advantageously to the method of treatment of nootropic disorders in mammals, using an effective amount of a compound of the invention, preferably in the form of above-cited pharmaceutical compositions.

The dosage of active compound administered is dependent on the species of warm-blooded animal (mammal), the body weight, age and individual condition, and on the form of administration.

A unit dosage for a mammal of about 50 to 70 kg may contain between about 10 and 500 mg of the active ingredient.

The following examples are intended to illustrate the invention and are not to be construed as being limitations thereon. Temperatures are given in degrees Centigrade. If not mentioned otherwise, all evaporations are performed under reduced pressure, preferably between about 2 and 13 kPa. The structure of final products, intermediates and starting materials is confirmed by analytical methods, e.g. microanalysis and spectroscopic characteristics (e.g. MS, IR, NMR). The compounds of formula I are hereinafter referred to as 3-amino-1-$R^1$-2-$R^2$-3-$R^3$-propyl(R)phosphinic acids.

EXAMPLE 1

To a solution of 1.0 g of ethyl 3-amino-2-(p-chlorophenyl)propyl(diethoxymethyl) phosphinate in 5 ml of methanol are added 2.5 ml of a 2 normal sodium hydroxide solution and the mixture is heated to a temperature of 80° for a period of 5 hours. After this time, the reaction is concentrated under reduced pressure, and the oily residue is passed down an Ion Exchange Resin (DOWEX® 50W-X8 H+) using de-ionised water as eluant. Ninhydrin-positive fractions are combined and evaporated to give 3-amino-2-(4-chlorophenyl)-propyl(diethoxymethyl)phosphinic acid, m.p. 175°–185° (dec.), $^{31}$P-NMR : $\delta = +31.6$ ppm ($D_2O$).

EXAMPLE 2

0.5 g of ethyl 3-amino-2-hydroxy-propyl(diethoxymethyl)phosphinate is dissolved in 5 ml of ethanol and this solution is added to a solution of 0.14 g of sodium hydroxide in 2 ml of water. This mixture is then heated to 60° for a period of 3 hours, cooled to room temperature and the solvent evaporated under reduced pressure. The oily residue is passed down an Ion Exchange Resin (DOWEX® 50W-X8 H+) using de-ionised water as eluant. Ninhydrin-positive fractions are combined and evaporated to give 3-amino-2-hydroxy-propyl(diethoxymethyl)phosphinic acid, m.p. 214°–215° (dec.), $^{31}$P-NMR : $\delta = +30.9$ ppm ($D_2O$).

The starting material may be prepared as follows:

To a solution of 25.0 g of ethyl (trimethylsilyl)diethoxymethylphosphonite in 200 ml of dry tetrahydrofuran is added 19.2 g of 2,3-epoxypropylphthalimide under an atmosphere of nitrogen. To this stirred mixture is added a catalytic amount of dry zinc chloride and the mixture is then refluxed for a period of 2 hours. After cooling, the solvent is evaporated under reduced pressure, the residue dissolved in 100 ml of chloroform, and stirred vigorously with 50 ml of water for a period of 0.5 hours. The organic layer is separated, dried over magnesium sulfate and the solvent is removed under reduced pressure. The residue is heated to 100° at 6 Pa of pressure for a period of 1 hour to leave as an oily residue ethyl 2-hydroxy-3-phthalimido-propyl(diethoxymethyl)phosphinate, $^{31}$P-NMR $\delta = +42.0$ and $+41.6$ ppm ($CDCl_3$).

To a solution of 1.0 g of ethyl 2-hydroxy-3-phthalimido-propyl(diethoxymethyl)phosphinate in 23 ml of isopropanol is added 4 ml of water. To this mixture is added 0.47 g of sodium borohydride and this is stirred for a period of 24 hours at room temperature. After this time 2.6 ml of glacial acetic acid are carefully added and the reaction heated to 80° for a period of 2 hours. After this time, the reaction is cooled to room temperature, the solvent evaporated under reduced pressure and the residue passed down a silica column using a mixture of one part ethyl acetate to one part ethanol as eluant. Ethyl 3-amino-2-hydroxy-propyl(diethoxymethyl)phosphinate is obtained as colourless oil, $^{31}$P = +45.8 and +45.2 ppm ($CDCl_3$).

EXAMPLE 3

A solution of 6.7 g of 3-(benzyloxycarbonylamino)-propyl(n-butyl) phosphinic acid in 125 ml of 36% hydrochloric acid is heated at reflux for 1.5 hour. The mixture is evaporated to an oil and the oil is co-evaporated with water (2×50 ml) to give a white solid. This solid is then dissolved in 50 ml of dry methanol, 1-3 ml of propylene oxide is added and the solution is stirred at room temperature. The precipitated product is collected by filtration and dried to give 3-aminopropyl(n-butyl) phosphinic acid, m.p. 231°-234° (dec.), $^{31}$P-NMR : $\delta = +44.6$ ppm ($D_2O$).

The starting material may be prepared as follows:

A solution of 5.0 g of 3-aminopropylphosphinic acid in 200 ml of water is cooled to 5°, and the pH adjusted to 9.5 with 2 molar sodium hydroxide solution. To this mixture is added 6.8 g of benzyl chloroformate whilst maintaining the pH and temperature. After the addition is complete the mixture is stirred for 3 hours at pH 9.5 at room temperature and left to stand overnight. The mixture is then extracted with 100 ml of ether and the aqueous layer stirred at 5° with an equal volume of chloroform. The mixture is acidified to pH 2, the chloroform layer separated, dried over magnesium sulfate and the solvent evaporated under reduced pressure. The oily product is triturated with ether to give a white solid, 3-(N-benzyloxycarbonylamino)propylphosphinic acid, m.p. 53°-55°, $^{31}$P-NMR : $\delta = +36.6$ ppm ($CDCl_3$).

To a solution of 3.0 g of 3-(N-benzyloxycarbonylamino)propylphosphinic acid in 50 ml of dry tetrahydrofuran is added 2.3 g of triethylamine. This mixture is stirred under an atmosphere of nitrogen for a period of 0.5 hours, and then 2.5 g of trimethylchlorosilane is added. This solution is stirred for a period of 1 hour during which time a precipitate forms. After this time, 7.6 g of 1-bromobutane is added and the reaction is refluxed for a period of 24 hours. The mixture is then allowed to cool to room temperature, 50 ml of water is added and the whole stirred for 1 hour. The mixture is extracted with 200 ml of chloroform, the organic layer dried over magnesium sulfate and the solvent evaporated under reduced pressure. The oily product is triturated with ether to give a white solid, being 3-(N-benzyloxycarbonylamino)- propyl(n-butyl)phosphinic acid, m.p. 116°-118°, $^{31}$P = +58.6 ppm ($CDCl_3$).

EXAMPLE 4

A solution of 3.3 g of lithium hydroxide monohydrate in 40 ml of water is added to a solution of 20 g of ethyl 3-aminopropyl(diethoxymethyl)phosphinate in 75 ml of ethanol. The mixture is stirred and approximately 25 ml of further water is added to obtain a clear solution. The solution is stirred at room temperature until the reaction is complete after approximately 48 hours. This can be monitored by $^{31}$P-NMR. Then the solution is evaporated to give a cloudy oil, to which are added 50 ml of ethanol. The insoluble inorganic solid is removed by filtration and the filtrate evaporated. The residual oily product which contains a little solid is triturated with acetone and the resulting solid filtered off ($^{31}$P NMR: $\delta = 33.98$ ppm; $D_2O$).

The filtrate from this is evaporated and again triturated with a little acetone to yield a second crop of product. Both crops are combined and dissolved in water. The solution is concentrated and extracted with chloroform to remove traces of starting material, then treated with charcoal. The solution is filtered to remove charcoal and reduced to a small volume. This crude product is then subjected to ion exchange chromatography (DOWEX® 50W-X8 H+ form) using de-ionised water as eluent. Fractions of 150 ml are collected. Fraction 44 and following fractions contain the 3-aminopropyl(diethoxymethyl)phosphinic acid, which is obtained in pure form after evaporation, m.p. 209°-210° (dec.).

EXAMPLE 5

To a solution of 8.0 g of isopropyl 3-aminopropyl(t-butyl) phosphinate in 80 ml of chloroform are added 11.7 ml of trimethylsilylbromide. The reaction mixture is stirred at 50° for 4 hours and then at room temperature overnight. Removal of chloroform and excess of trimethylsilylbromide under reduced pressure gives an oil which is taken up in ethanol. Propylene oxide is added and the white solid is filtered off and dried over phosphorous pentoxide to yield 3-aminopropyl(t-butyl)-phosphinic acid ×0.15 $H_2O$, m.p. 253°-255°.

The starting material is prepared as follows:

A mixture of 24.7 g of isopropanol and 17.2 g of triethylamine in 35 ml of diethylether is added drop by drop to 30 g of t-butyldichlorophosphine in 100 ml diethylether. The temperature is kept between 5 to 10°. The solid is filtered off and the filtrate evaporated. The crude oil is purified by distillation to yield t-butylphosphonous acid-isopropylester as an oil, b.p. 82°/2 kPa, $n_D^{20} = 1.4222$.

To 15.7 g of t-butylphosphonous acid-isopropylester in 6.3 ml of acrylonitrile are added 21 ml of sodium isopropylate (0.25 molar). After the exothermic reaction (the temperature rises to 100°) the suspension is filtered, the filtrate evaporated and the residue distillated to yield isopropyl 2-cyanoethyl(t-butyl)phosphinate as an oil, b.p. 121°/8 Pa, $n_D^{20} = 1.4480$.

A mixture of 11.0 g of isopropyl 2-cyanoethyl(t-butyl)phosphinate, 17.0 g of ammonia and 1.7 g of Raney-Nickel in 110 ml of ethanol is hydrogenated during 5 hours. The catalyst is filtered off and the solvent removed by evaporation. The crude oil is purified by Kugelrohr-distillation to yield isopropyl 3-aminopropyl(t-butyl)phosphinate as an oil, b.p. 155°/1 Pa, $n_D^{20} = 1.4600$.

EXAMPLE 6

7.0 g of isopropyl 3-aminopropyl(n-propyl)phosphinate and 40 ml of 20% hydrochloric acid are stirred at reflux temperature overnight. The reaction mixture is evaporated to dryness, taken up in methanol and treated with propylene oxide. The white solid is filtered off and dried over phosphorous pentoxide to yield 3-aminopropyl(n-propyl)phosphinic acid ×0.1 $H_2O$ as white crystals, m.p. 210°-213°.

3-Aminopropyl(n-propyl)phosphinic acid can also be prepared from the same starting material by silylation with trimethylsilylbromide and subsequent treatment with propylene oxide in ethanol, m.p. 213°-215°.

The starting materials isopropyl 3-aminopropyl(n-propyl)phosphinate, b.p. 155°/6 Pa, $n_D^{20} = 1.4571$; isopropyl 2-cyanoethyl(n-propyl)phosphinate, b.p. 132°/40 Pa, $n_D^{20} = 1.4470$; and n-propylphosphonous acid-isopropylester, b.p. 93°/2.8 kPa; $n_D^{20} = 1.4241$ are prepared in a similar way as described in the preceding example starting from n-propyldichlorophosphine.

EXAMPLE 7

A mixture of 7.73 g of isopropyl 3-aminopropyl(ethyl)-phosphinate and 40 ml of 20% hydrochloric acid is refluxed with stirring for 14 hours. The clear solution is evaporated to dryness and the residue is recrystallized from methanol/propylenoxide to give 3-aminopropyl(ethyl)phosphinic acid as a white solid, m.p. 233°–239°; $^1$H-NMR ($D_2O$): 0.4–1.8 (m, 9H, $PCH_2CH_2$ and $PCH_2CH_3$); 2.7 (t, 2H, $NCH_2$); 4.55 (s, 3H, OH, $NH_2$).

The starting materials are prepared as follows:

To a solution of 262 g of ethyldichlorophosphine in 1200 ml of diethylether is added with stirring and cooling with ice at 5°–10° a solution of 370 ml of isopropanol and 280 ml of triethylamine in 400 ml of diethylether. The reaction is exothermic. After stirring for 12 hours at 20° the white precipitate is filtered off and the filtrate is fractionally distilled. There is obtained ethylphosphonous acid-isopropylester as a colorless liquid, b.p. 80°–85°/26 kPa.

To 34 g of ethylphosphonous acid-isopropylester and 16.45 ml of acrylonitrile is added with stirring 40 ml of isopropanol containing 0.25 mol of sodium isopropylate. The reaction is exothermic. After 1 hour stirring at 20° the mixture is fractionated. There is obtained isopropyl 2-cyanoethyl(ethyl)phosphinate as a colorless oil, b.p. 102°–104°/10 Pa.

To 34.1 g of isopropyl 2-cyanoethyl(ethyl)phosphinate in 500 ml of isopropanol are added 60 ml of liquid ammonia and 6.8 g of Raney-Nickel. The mixture is heated to 80° and treated with hydrogen at 100 bar. After 1½ hours hydrogen-uptake stops. The reaction mixture is filtered and the filtrate distilled to give isopropyl 3-aminopropyl(ethyl)phosphinate as a colorless oil, b.p. 75°/13 Pa.

EXAMPLE 8

A mixture of 1.5 g of 3-aminopropyl(phenyl)phosphinic acid in 10 ml of water and 7.9 ml of 1N hydrochloric acid is treated with hydrogen at 25° in the presence of 0.2 g of Nishimura-catalyst (Rh/$PtO_2$). After 1.2 hours hydrogen up-take stops. The reaction mixture is filtered and the filtrate evaporated to dryness. The residue is recrystallized from methanol/propylenoxide to give 1.2 g of 3-aminopropyl(cyclohexyl)phosphinic acid ×0,4 mol hydrochloric acid as a white solid, m.p. 202°–203°.

The starting materials are prepared as follows:

To a solution of 270 ml of phenyldichlorophosphine in 1000 ml of diethylether is added with stirring and cooling with ice a solution of 280 ml of ethanol and 280 ml of triethylamine in 500 ml of diethylether. After stirring for 14 hours at 20° the precipitate is filtered off and the filtrate is fractionally distilled. There is obtained phenylphosphonous acid-ethylester as a colorless liquid, b.p. 83°–85°/6 Pa.

To 42.45 g of phenylphosphonous acid-ethylester and 16.45 ml of acrylonitrile are added with stirring 5 ml of sodium ethylate (1 molar). The reaction is exothermic. After 1 hour stirring at 20° the mixture is fractionally distilled. There is obtained ethyl 2-cyanoethyl(phenyl)phosphinate as a colorless oil, b.p. 134°–136°/7 Pa.

To 22.72 g of ethyl 2-cyanoethyl(phenyl)phosphinate in 400 ml of ethanol are added 34 g of liquid ammonia and 4.5 g of Raney-Nickel. The mixture is heated to 80° and treated with hydrogen at 100 bar. After 30 minutes hydrogen up-take stops. The reaction mixture is filtered and the filtrate distilled to give ethyl 3-aminopropyl(phenyl)phosphinate as a colorless oil, b.p. 110°/13 Pa.

A mixture of 6.83 g of ethyl 3-aminopropyl(phenyl)phosphinate and 30 ml of 20% hydrochloric acid is refluxed with stirring for 4 hours. The clear solution is evaporated to dryness and the residue is recrystallized from methanol/propylenoxide to give 3-aminopropyl(phenyl)phosphinic acid as a white solid, m.p. 298°–300°.

EXAMPLE 9

A mixture of 14.76 g (0.12 mol) of 3-aminopropylphosphonous acid and 96.72 g (0.6 mol) of hexamethyldisilazane is refluxed under an atmosphere of argon with stirring for 16 hours to give a solution. To this solution are added at reflux 60 ml of diethyleneglycol dimethylether and the solution is refluxed for additional 2 hours. The reaction is cooled to 120° and 38.75 g (0.3 mol) of N-ethyl-diisopropyl-amine are added within 20 minutes followed by addition of 54.06 g (0.3 mol) of isobutyl iodide over a period of 20 minutes. The reaction mixture is heated with stirring for 22 hours. After cooling to 10°, the white precipitate is filtered off and the filtrate is evaporated under reduced pressure. The clear solution is cooled, diluted with dichloromethane (300 ml) and extracted three times with 2N hydrochloric acid (3×100 ml). The combined hydrochloric acid-extracts are evaporated in vacuo to dryness, and re-evaporated twice with water (2×100 ml) to give a white solid, which is suspended in 600 ml of acetone and stirred for 1 hour at 20°. 3-Aminopropyl(isobutyl)phosphinic acid hydrochloride (25.3 g), m.p. 149°=155°, is isolated by filtration. After recrystallisation from n-propanol/acetone (200/100 ml) pure 3-aminopropyl(isobutyl)phosphinic acid hydrochloride of m.p. 154°–156°, is obtained. 15.4 g of 3-aminopropyl(isobutyl)phosphinic acid hydrochloride are dissolved in 75 ml of methanol and 300 ml of propylenoxide are added with stirring. After standing overnight at 4°, a white solid precipitates. The precipitate is collected by filtration and recrystallized from n-propanol to give pure 3-aminopropyl(isobutyl)phosphinic acid, m.p. 250°–253° (dec.).

EXAMPLE 10

In a manner analogous to that described in Example 9, 3-aminopropyl(n-hexyl)phosphinic acid, m.p. 242°–246°, hydrochloride: m.p. 196°–198°, is obtained with n-bromohexane at 130°, 22 hours.

EXAMPLE 11

In a manner analogous to that described in Example 9, 3-aminopropyl(allyl)phosphinic acid, m.p. 230°–234° (dec.), hydrochloride: m.p. 140°–142°, is obtained by reaction with allylbromide at 60°, 16 hours.

EXAMPLE 12

In a manner analogous to that described in Example 9, 3-aminopropyl(n-pentyl)phosphinic acid m.p. 232°–236°, hydrochloride: m.p. 192°–194°, is obtained by reaction with n-bromopentane at 120°, 16 hours.

EXAMPLE 13

In a manner analogous to that described in Example 9, 3-aminopropyl(n-heptyl)phosphinic acid, m.p. 232°–236° (dec), hydrochloride: m.p. 190°–192°, is obtained by reaction with n-bromoheptane at 120°, 16 hours.

EXAMPLE 14

In a manner analogous to that described in Example 9, 3-aminopropyl(but-3-enyl)phosphinic acid, m.p. 215°–220°, hydrochloride: m.p. 170°–172°, is obtained by reaction with 4-bromo-1-butene at 95°, 6 hours.

EXAMPLE 15

In a manner analogous to that described in Example 9, 3-aminopropyl(n-decyl)phosphinic acid, m.p. 225°–230°, hydrochloride m.p. 185°–190°, is obtained by reaction with n-bromodecane at 120°, 20 hours.

EXAMPLE 16

In a manner analogous to that described in Example 9, 3-aminopropyl(isopentyl)phosphinic acid, m.p. 238°–240° (dec.), hydrochloride: m.p. 159°–161°, is obtained by reaction with 1-bromo-3-methylbutane at 120°, 22 hours.

EXAMPLE 17

In a manner analogous to that described in Example 9, 3-aminopropyl(cyclopropylmethyl)phosphinic acid $\times 0,16H_2O$, m.p. 235°–238° (dec.), hydrochloride: m.p. 144°–146°, is obtained by reaction with bromomethylcyclopropane at 100°, for 22 hours.

EXAMPLE 18

In a manner analogous to that described in Example 9, (1-methyl-3-aminopropyl)(n-butyl)phosphinic acid $\times 0,2H_2O$, m.p. 212°–215°, hydrochloride: m.p. 137°–139°, is obtained by reaction of 1-methyl-2-aminopropylphosphonous acid with n-butylbromide at 100°, 48 hours.

EXAMPLE 19

In a manner analogous to that described in Example 9, 3-aminopropyl(pent-3-ynyl)phosphinic acid $\times 0,2H_2O$, m.p. 220°–224° (dec.), hydrochloride: m.p. 174°–176°, is obtained by reaction with 5-iodopent-2-yne at 60°, 16 hours.

EXAMPLE 20

In a manner analogous to that described in Example 9, 3-aminopropyl(but-3-ynyl)phosphinic acid, m.p. 214°–218°, hydrochloride: m.p. 148°–150°, is obtained by reaction with 4-iodobut-1-yne at 90°, 16 hours.

EXAMPLE 21

In a manner analogous to that described in Example 9, 3-aminopropyl(2-ethoxyethyl)phosphinic acid $\times 0,14H_2O$ m.p. 202°–208°, is obtained by reaction with (2-bromoethoxy)ethane at 100°, 16 hours.

EXAMPLE 22

In a manner analogous to that described in Example 9, 3-aminopropyl(2-methylbutyl)-phosphinic acid $\times 0.1H_2O$, m.p. 248°–254°, is obtained by reaction with 2-methylbutyliodide at 100°, 16 hours.

2-Methylbutyliodide may be prepared in the following manner.

17.63 g (0.20 mol) of 2-methyl-butanol is added slowly during 20 minutes with stirring to a mixture of 43.3 g (0.227 mol) of toluene-p-sulphonylchloride in 20 ml of dry pyridine, keeping the temperature below 25° by external cooling. After stirring for 2 hours at 20°, the mixture is poured into ice-water and extracted with ether. The ether layer is washed subsequently with 2 N sulphic acid, water and saturated sodium hydrogencarbonate solution. After drying over sodium sulphate, filtration and evaporation in vacuo 2-methylbutyl toluene-p-sulphonate are obtained as a yellow oil.

45.99 g (0.189 mol) of 2-methylbutyl toluene-p-sulphonate are dissolved in 290 ml of acetone, 34.7 g (0.23 mol) of sodium-iodide is added at 20° and the mixture is stirred for 2 hours under reflux. After cooling to 0° the separated sodium toluene-p-sulphonate is removed by filtration, and the solvent is evaporated through a 15 cm Vigreux-column at atmospheric pressure.

The crude product is dissolved in ether and washed with 10% sodium thiosulphate solution, dried over sodium sulphate and filtered off. Evaporation of the solvent through a 15 cm Vigreux column, followed by fractionational distillation gives 2-methylbutyliodide; b.p. 93°/200 mbar.

EXAMPLE 23

In a manner analogous to that described in Example 9, 3-aminopropyl-(3-ethoxypropyl)-phosphinic acid $\times 0,1H_2O$, m.p. 210°–218°; hydrochloride: m.p. 161°–165°, is obtained by reaction with 2-ethoxypropyliodide at 130°, 16 hours. 3-Ethoxypropyliodide may be prepared in the following manner.

20.8 g (0.20 mol) of 2-ethoxypropanol are added slowly during 20 minutes with stirring to a mixture of 43.3 g (0.227 mol) of toluene-p-sulphonylchloride and 20 ml of dry pyridine. The temperature of the reaction mixture is kept at 20° with external cooling. After stirring for 2 hours at 20°, the mixture is poured into ice-water and extracted with ether. The ether layer is washed with 2N sulphuric acid, with water and with saturated sodium hydrogencarbonate solution. After drying over sodium sulphate, filtration and evaporation in vacuo, 2-ethoxypropyl toluene-p-sulphonate is obtained as a yellow oil.

A solution of 51.5 g (0.199 mol) of 2-ethoxypropyl toluene-p-sulphonate and 36.5 g (0.243 mol) of sodium iodide in 250 ml of acetone is stirred under reflux for 2 hours. After cooling to 10°, the separated sodium toluene-p-sulphonate is removed by filtration, and the solvent is evaporated through a 15 cm Vigreux-column at atmospheric pressure. The crude product is dissolved in ether and washed with a 10% (b.w.) solution of sodium thiosulphate. Drying over sodium sulphate, filtration and evaporation of the solvent through a 15 cm Vigreux column, followed by fractional distillation yields 3-ethoxypropyliodide, b.p. 97°/40 mbar.

EXAMPLE 24

In a manner analogous to that described in Example 9, 3-aminopropyl(3-methoxypropyl)phosphinic acid $\times 0,25H_2O$; m.p. 197°–203°, hydrochloride: m.p. 146°–148°, is obtained by reaction with 2-methoxypropyliodide at 115°, 40 hours.

EXAMPLE 25

In a manner analogous to that described in Example 9, 3-aminopropyl(but-2-ynyl)phosphinic acid $\times 1,2H_2O$; m.p. 110°–115°, hydrochloride m.p. 154°–158°, is obtained by reaction with 1-bromo-2-butyne at 90° for 16 hours.

EXAMPLE 26

In a manner analogous to that described in Example 9, 3-aminopropyl[2-(2-ethoxyethoxy)ethyl]phosphinic acid ×0.16H₂O m.p. 215°–225°, is obtained by reaction with [2-(2-ethoxyethoxy)ethyl]iodide.

EXAMPLE 27

In a manner analogous to that described in Example 9, 3-aminopropyl(4,4,4-trifluorobutyl)phosphinic acid, m.p. 237°–241° (decomp.), hydrochloride: m.p. 144°–146°, is obtained by reaction with 4,4,4-trifluorobutyliodide at 95°, 16 hours.

EXAMPLE 28

In a manner analogous to that described in Example 9, 3-aminopropyl(2-methylthioethyl)phosphinic acid is obtained by reaction with 1-chloro-2-methylthio-ethane at 100°, 16 hours.

EXAMPLE 29

In a manner analogous to that described in Example 9, 3-aminopropyl(methylthiomethyl)phosphinic acid is obtained by reaction with methylthiomethyl chloride at 75°, 16 hours.

EXAMPLE 30

In a manner analogous to that described in Example 9, 3-aminopropyl(2-phenylethyl)phosphinic acid, m.p. 265°–270° is obtained by reaction with 2-phenylethylbromide at 120°, 16 hours.

EXAMPLE 31

In a manner analogous to that described in Example 9, 3-aminopropyl(2-methylallyl)phosphinic acid, m.p. 140°–143°, is obtained by reaction with methallyl chloride at 63°, 24 hours.

EXAMPLE 32

A solution of 2.4 g of 3-benzyloxycarbonylaminopropyl(dodecyl) phosphinic acid in 50 ml of 36% hydrochloric acid is refluxed for 3 hours. During this time, a white precipitate is formed. After cooling to room temperature the acid is removed by co-evaporation with 6×50 ml of water on a rotary evaporator. The crude product is then dissolved in 50 ml of ethanol and stirred with 5 ml of propylene oxide. Filtration and drying gives 3-aminopropyl(dodecyl) phosphinic acid as a white solid m.p. 175°–7°. $^{31}$P-NMR=43.0 ppm (NaOD).

The starting material can be prepared as follows:

A solution of 1.30 g of dodecene in 6 ml of dry toluene is heated to 80° under an atmosphere of argon. To this solution a suspension of 2.0 g of 3-benzyloxycarbonylaminopropylphosphonous acid in 30 ml of dry tolpene containing 0.6 g of t-butylcyclohexylperdicarbonate is added within 15 minutes. The reaction mixture is then stirred at 80° for 2 hours. An additional amount of 0.6 g of the radical initiator is added and stirring at 80° is continued for 2 hours. Then, the reaction mixture is cooled to room temperature and the solvent is removed by means of a rotary evaporator. The residue is triturated with petroleum ether (60°–80°), filtered and dried to give 3-benzyloxycarbonylaminopropyl(dodecyl)phosphinic acid as a white solid, m.p. 115°–6°; $^{31}$P-NMR: δ = +58.7 ppm (CDCl₃).

EXAMPLE 33

To a solution of 5.7 g (0.0224 mol) of isopropyl 3-aminopropyl(benzyl)phosphinate in 50 ml of chloroform 9.91 ml (0.0922 mol) of trimethylsilylbromide are added raising the temperature to 44°. The reaction mixture is stirred at 50° for 4 hours and then at room temperature overnight. Removal of the chloroform and excess trimethylsilylbromide under reduced pressure yields an oil which is taken up in isopropanol and 20 ml of propylene oxide. After stirring for 10 minutes, a white solid precipitates. The solid is filtered off and dried over phosphorous pentoxide yielding 3-aminopropyl(benzyl)phosphinic acid, m.p. 278°–280°.

The starting material can be prepared from benzyldichloro-phosphine via benzylphosphonous acid isopropylester, b.p. 113° (1 mbar), isopropyl 2-cyanoethyl(benzyl)phosphinate, m.p. 69°–72°, and isopropyl 3-aminopropyl(benzyl)phosphinate, b.p. 113° (1 mbar).

EXAMPLE 34

A suspension of 1,23 g (10 mmol) of 3-aminopropylphosphonous acid in 10.4 ml (50 mmol) of hexamethyldisilazane is heated to reflux under argon for 24 hours. 5 ml of diethylene glycol dimethyl ether are added to the clear solution obtained and the mixture is heated for additional 2 hours and then cooled to 0°. 8.5 ml (50 mmol) of N-ethyl-N,N-diisopropyl-amine are added, followed by slow addition of 3.8 ml (50 mmol) of propargyl bromide over a period of 40 minutes. The mixture is stirred for 1 hour at 0° and 4 hours at room temperature, filtered and evaporated under high vacuum. The residue is dissolved in 10 ml of dichloromethane and extracted with 3×10 ml of 1N hydrochloric acid solution. The water layer is evaporated under high vacuum and the residue obtained dissolved in 4 ml of methanol at 0°. 20 ml of propylene oxide are added during a period of 1 hour, after which time a crude product precipitates. Chromatography (silicagel Merck 230–400 ASTM, methanol) followed by recrystallization (methanol/ether) yields 3-aminopropyl(propargyl)phosphinic acid, m.p. 172°–173°.

EXAMPLE 35

To a solution of 0.90 g (4.0 mmol) of 3-aminopropyl(diethoxymethyl)phosphinic acid in 10 ml of glacial acetic acid at 0° there are added 0.38 ml (4,4 mmol) of ethane-1 2-dithiol, followed by addition of 2 ml of concentrated hydrochloric acid over a period of 5 min. The mixture is allowed to warm to room temperature and is then stirred for 18 hours. After removal of acetic and hydrochloric acids under high vacuum, the residue is chromatographed (Opti-Up ® C₁₂ 50%, water) and recrystallized from methanol to yield 3-aminopropyl(1,3-dithiolan-2-yl)phosphinic acid, m.p. 272°–274°.

EXAMPLE 36

To 590 mg (2.20 mmol) of lithium hydroxide monohydrate in 1.1 ml of water a solution of 2 mmol of ethyl 3-aminobutyl(diethoxymethyl)phosphinate in 2.1 ml of ethanol, and then 1 ml of water are added. The mixture is stirred 48 hours at room temperature and evaporated in vacuo. 3 ml of water are added to dissolve the precipitate formed. Then 85 mg of 84% (b.w.) phosphoric acid are added slowly and the suspension is stirred for 18 hours at room temperature. After filtration of the precipitate through celite, evaporation to dryness, chromatography (Opti-Up ® C₁₂ 50%, H₂O) and recrystallisation from ethanol, 3-aminobutyl(diethoxymethyl)phosphinic acid, m.p. 225°–228°, is obtained.

The starting material may be obtained as follows:

A mixture of 2.7 g of ethyl trimethylsilyldiethoxymethylphosphonite and 0.7 g of methyl vinyl ketone is warmed to 50° for 1 hour under an atmosphere of nitrogen. Then 10 ml of water are added and the mixture is stirred for additional 30 minutes. The residue is extracted thrice with 50 ml of chloroform, the organic phases are combined, dried over magnesium sulphate, filtered and evaporated to dryness. The residue is then distilled to yield ethyl 3-oxobrtyl(diethoxymethyl)phosphinate, b.p. 130°–5° (13.6 mbar).

A mixture of 1.0 g of ethyl 3-oxobutyl(diethoxymethyl)phosphinate 2.85 g of ammonium acetate and 0.16 g of sodium cyanoborohydride in 20 ml of methanol is stirred for 2.5 hours. After standing overnight, the pH is adjusted to pH 5,6 with 2N hydrochloric acid. The mixture is then evaporated to dryness. 20 ml of water are added and the mixture is washed 3 times with 20 ml of diethyl ether. The aqueous layer is adjusted to pH 12 with potassium hydroxide and extracted 4 times with 25 ml of chloroform. The organic layers are combined, dried, filtered and evaporated to dryness yielding ethyl 3-asinobutyl(diethoxymethyl)phosphinate, $^{31}$P-NMR spectrum: $\delta = +46.0$ ppm (CDCl$_3$).

EXAMPLE 37

In an analogous manner, by saponification with lithium hydroxide in aqueous ethanol 3-amino-1-(p-chlorophenyl)-propyl(diethoxymethyl)phosphinic acid is obtained as a yellow oil; $^1$H-NMR (CDCl$_3$): δ7.2–7.4 (m, 4), 4.1 (d, 1, J=6.5 Hz), 3.7 (m, 2), 3.6 (m, 2), 3.3 (t, 1, J=7.5 Hz), 3.1 (m, 2), 3.0 (m, 4), 2.7 (m, 2), 2.2 (broad, 2), 1.2 (m, 6).

The starting material, ethyl 3-amino-1-(p-chlorophenyl)propyl(diethoxymethyl)phosphinate, may be obtained as follows:

A mixture of 25.8 g of ethyl diethoxymethylphosphinate, 18.0 g of 4-chlorcinnamoyl nitrile and 100 ml of ethanol is added dropwise at 0 to 5° to a stirred solution of 1.2 g of sodium hydride (50% suspension in mineral oil) in 30 ml of ethanol. Then the ethanol is evaporated, the residue is dissolved in 100 ml of chloroform and washed twice with 25 ml of water, the organic phase is dried over magnesium sulfate, filtered and evaporated to yield 20 g of ethyl 1-(p-chlorophenyl)-2-cyanoethyl(diethoxymethyl) phosphinate as an oil, $^{31}$P-NMR: δ+37.8 and +37.9 ppm (CDCl$_3$).

A solution of 20.0 g of ethyl 1-(p-chlorophenyl)-2-cyano-ethyl(diethoxymethyl)phosphinate in 131 g of a 8% (b.w.) ethanolic solution of ammonium is stirred with 8.5 ml of Raney Nickel in 85 ml of ethanol, and hydrogenated until hydrogen uptake ceased. Filtration and evaporation then gives ethyl 3-amino-1-(p-chlorophenyl)propyl(diethoxymethyl)phosphinate as an oil.

EXAMPLE 38

To a stirred solution of 0.05 g of lithium hydroxide monohydrate in 7.7 ml of water, is added a solution of 4.37 g of ethyl 3-aminopropyl(di-n-propyloxymethyl)-phosphinate in 16.2 ml of ethanol. A slight exothermic reaction ensues and the reaction mixture becomes cloudy. A further 2 ml of water are added and the clear solution stirred at room temperature for 5 days. After this time the mixture is concentrated in vacuo at 55° and the residue redissolved in water and extracted with 3×10 ml of dichloromethane. The aqueous layer is again evaporated to dryness and the residue dissolved in 20 ml of water and treated with 0.51 ml of 85% phosphoric acid. After stirring overnight, the solid is removed by filtration. Evaporation of the filtrate and crystallisation of the residue from ethanol/ether affords 3-aminopropyl(di-n-propyloxymethyl) phosphinic acid, m.p. 223°–225°, as a white solid.

The starting material may be prepared as follows:

A mixture of 6.6 g of hypophosphorous acid (95% solution in water) and 86 g of tri-n-propyl orthoformate is treated with 0.77 ml of trifluoracetic acid. The two-phase mixture is stirred at room temperature for 48–72 hours until the reaction is complete. This can be monitored by $^{31}$P-NMR or thin layer chromatography. The reaction mixture is diluted with 200 ml of dichloromethane and washed twice with 150 ml of a saturated aqueous solution of sodium bicarbonate. After drying the dichloromethane layer over anhydrous magnesius sulphate and removal of the solvent in vacuo, a colorless oil is obtained which after distillation affords di-n-propyloxymethylphosphonous acid n-propyl ester, b.p. 45°/2 ×10$^4$ mbar.

A solution of sodium ethoxide in absolute ethanol (0.48 g of sodium metal in 15 ml of absolute ethanol) is cooled to 0° under nitrogen or argon. A solution of 2.72 g of acrylonitrile and 12.2 g of di-n-propyloxymethylphosphonous acid n-propylester in 50 ml of absolute ethanol is added at such a rate that the temperature does not exceed 5°. After the addition is completed, the solution is allowed to warm to room temperature and stirred overnight. After addition of 1.22 g of glacial acetic acid, the reaction mixture is concentrated in vacuo. The residue is partitioned between ethyl acetate and water and the organic phase separated. After drying over anhydrous magnesium sulphate the solvent is evaporated in vacuo to afford an oil. Chromatography on silica-gel yields ethyl 2-cyanoethyl(di-n-propyloxymethyl)phosphinate as a colourless oil.

A mixture of 4,35 g of ethyl 2-cyanoethyl(di-n-propyloxymethyl)phosphinate, 10 g of ammonia and 2.3 g of Raney-Nickel :n 170 ml of ethanol is hydrogenated for 10.5 hours. The catalyst is filtered off and the solvent is removed by evaporation. The crude oil is purified by distillation to yield ethyl 3-aminopropyl(di-n-propyloxymethyl)phosphinate as a colourless oil.

EXAMPLE 39

In a manner analogous to that described in Example 38, 3-aminopropyl(diisopropyloxymethyl)phosphinic acid, m.p. 175° m.p. (dec.) can be prepared.

The starting materials: Diisopropyloxymethylphosphonous acid isopropylester, b.p. 48°, 2×10$^{-4}$ mbar; ethyl 2-cyanoethyl(diisopropyloxymethyl)phosphinate and ethyl 3-aminopropyl(diisopropyloxymethyl)phosphinate are prepared as described in Example 38 from hypophosphorous acid and triisopropyl orthoformiate.

EXAMPLE 40

In a manner analogous to that described in Example 38, 3-aminopropyl(di-n-butyloxymethyl)phosphinic acid, m.p. 221°–224°, can be prepared.

The starting materials: di-n-butyloxymethylphosphonous acid n-butylester, b.p. 75°, 2.0×15$^{-4}$ mbar; ethyl 2-cyanoethyl(di-n-butyloxymethyl)phosphinate and ethyl 3-aminopropyl(di-n-butoxymethyl)phosphinate are prepared as described in Example 38 from hypophosphorous acid and tri-n-butyl orthoformate.

EXAMPLE 41

To a stirred solution of 0.57 g of lithium hydroxide monohydrate hydrate in 10 ml of water is added a solution of 2.0 g of ethyl-3-amino-propyl(tetrahydrofuran-2-yl) phosphinate in 20 ml of ethanol. A slight exothermic reaction ensues and the reaction mixture becomes turbid. A further 5 ml of water is added and the then clear solution stirred for 3 days at room temperature. After this time, the reaction mixture is concentrated in vacuo at 55°. The residue is re-dissolved in water and washed with 3×10 ml of dichloromethane. The aqueous layer is again evaporated to dryness and the residue dissolved in 10 ml of water and treated with 0.65 ml of 85% phosphoric acid in 2 ml of water. After stirring overnight, the solid is removed by filtration. Evaporation of the filtrate and crystallisation of the residue from methanol/ether affords 3-aminopropyl(tetrahydrofuran-2-yl)phosphinic acid, m.p. 222°–223° (dec.), as a white solid.

The starting material can be prepared either from diethoxymethyl- or diethoxyethylphosphonous acid as follows:

A solution of 12.7 g of diethoxymethylphosphonous acid ethyl ester and 6.95 g of 4-chlorobutanal in 10 ml of absolute ethanol is cooled to 0° under inert gas. Ethanolic sodium ethoxide (from 1.5 g of sodium metal and 20 ml of absolute ethanol) is added dropwise so that the temperature does not rise above 5°. After the addition is completed, the reaction mixture is warmed to room temperature and stirred for 20 hours. After this time a suspension results and the solvent is removed in vacuo. The residue is dissolved in dichloromethane/water and the organic layer separated and washed with a further 20 ml of water. After drying with anhydrous magnesium sulphate and removal of the solvent in vacuo O-ethyl-P-Piethoxymethyltetrahydrofuran-2-yl-phosphinate, b.p. 125°/1 ×10$^{-2}$ mbar, is obtained.

A suspension of 5.32 g of 0-ethyl-P-ciethoxymethyl-tetrahydrofuran-2-yl phosphinate in 50 ml of 6.0M aqueous hydrochloric acid is heated to 100° for 16 hours. After this time the solution is evaporated to dryness in vacuo and the residue co-evaporated in vacuo with 5×20 ml of water followed by 5×20 ml of water followed by 5×10 ml of absolute ethanol. Drying the residue over phosphorous pentoxide in high vacuum at room temperature yields P-tetrahydrofuran-2-yl-phosphonous acid; $^1$H-NMR (CDCl$_3$): δ11.24 (1 H, s exchanges with D$_2$O), 6.97 (1 H, d, J=557 Mz), 4.07 (1 H, a). 3.90 (2 H, t, CH$_2$O), 2.15 (2 H, m), 1.99 (2 H, m).

A solution of 2.6 g of P-tetrahydrofuran-2-yl-phosphonous acid in 20 ml of anhydrous dichloromethane is cooled to 5° under inert gas and treated with 2.03 g of triethylamine. A dichloromethane solution of 2.17 g of ethyl chloroformate is added dropwise whereupon an exothermic reaction and a gas evolution ensues. The suspension is warmed to room temperature and stirred for 3 hours. The reaction mixture is then diluted with dichloromethane and washed with water. Drying of the organic phase with anhydrous magnesium sulphate and removal of the solvent in vacuo affords P-tetrahydrofuran-2-ylphosphonous acid ethyl ester, b.p. 90°/8×10$^{-2}$ mbar.

A mixture of 0.68 g of acrylonitrile and 2.11 g of tetrahydrofuran-2-yl phosphonous acid ethyl ester in 5 ml of absolute ethanol is cooled to 0° under argon and treated, dropwise, with an ethanolic solution of sodium ethoxide (from 0.15 g of sodium metal and 15 ml of absolute ethanol) at such a rate so that the temperature does not exceed 5° (extremely exothermic). After the addition is completed the reaction mixture is stirred at room temperature for 30 minutes and 0.4 g of glacial acetic acid are added. The solvent is removed in vacuo and the residue partitioned between dichloromethane water. The organic layer is dried with anhydrous magnesium sulphate and removed in vacuo to afford ethyl 2-cyanoethyl(tetrahydrofuran-2-yl)-phosphinate; $^1$H-NMR (CDCl$_3$): δ4.15 (3 H, m), 3.90 (2 H, m), 2.72 (2 H, m, CH$_2$CN), 2.34–1.87 (6 H, m), 1.32 (3 H, m, CH$_3$).

A solution of ethyl-2-cyanoethyl(tetrahydrofuran-2-yl)phosphinate in absolute ethanol containing 10% by weight of ammonia is hydrogenated over Raney-Nickel for 2.5 hours. The catalyst is removed by filtration and the solvent removed in vacuo to afford ethyl-3-aminopropyl(tetrahydrofuran-2-yl) phosphinate; $^1$H-NMR (CDCl$_3$): δ4.24 (4 H, m), 3.95 (1 H, m), 2.88 (2 H, sharpens on D$_2$O addition: CH$_2$NH$_2$), 2.40–1.75 (6 H, m), 1.32 (3 H, t).

A solution of 2.10 g of 1,1-diethoxysthylphosphonous acid ethyl ester and 1.06 g of 4-chlorobutanal in 10 ml of absolute ethanol is cooled to 0° under inert gas. Ethanolic sodium ethoxide (from 0.23 g of sodium metal and 20 ml of absolute ethanol) is added dropwise so that the temperature does not exceed 5°. After the addition is completed, the reaction mixture is warmed to room temperature and stirred for 20 hours. After this time a suspension results and the solvent is removed in vacuo. The residue is dissolved in dichloromethane/water and the organic layer separated and washed with a further 20 ml of water. After drying of the organic phase with anhydrous magnesium sulphate and evaporation in vacuo ethyl 1,1-diethoxyethyl(tetrahydrofuran-2-yl)phosphinate is obtained as a clear oil, b.p. 110°/1 ×10$^{-2}$ mbar.

A solution of 1 g of ethyl 1,1-diethoxymethyl(tetrahydrofuran-2-yl)phosphinate in 10 ml of dichloromethane containing 1% (b.v.) of ethanol is treated with 0.71 g of trimethylsilylchloride. The faintly cloudy solution is stirred overnight at room temperature after which time thin layer chromatography indicates complete reaction. Removal of the solvent in vacuo affords a colourless oil which after distillation yields P-tetrahydrofuran-2-yl-phosphonous acid ethyl ester, b.p. 90°/8 ×10$^{-2}$ mbar.

Further elaboration of P-tetrahydrofuran-2-yl-phosphonous acid ethyl ester to ethyl 2-cyanoethyl(tetrahydrofuran-2-yl)phosphinate and ethyl 3-aminopropyl(tetrahydrofuran-2-yl)phosphinate proceeds in a manner identical to that described in example 41.

EXAMPLE 42

A suspension of 2.46 g of 3-aminopropylphosphonous acid in 20 ml of hexamethyldisilazane is heated to reflux under an inert gas for 24 hours. The resulting clear solution is cooled to room temperature and 14.8 g of freshly distilled n-butyraldehyde are added. An exothermic reaction ensues, the reaction temperature, rising to approximately 60° C. The reaction mixture is stirred for 1 hour at a temperature between 10° and 60°. After cooling to room temperature, the volatile materials are removed in vacuo to yield a colourless oil. This oil is dissolved in water and stirred at room temperature for 1 hour and the aqueous layer is evaporated to dryness at 55°. A semi-solid residue is obtained which is dissolved in 50 ml of 2.0M aqueous hydrochloric acid and washed with dichloromethane, (3×100 ml), and ether (1×100 ml). After removal of the water the white solid is co-evaporated with water (10×50 ml), and then with 10×50 ml of absolute ethanol. Crystallisation of the residue form ethanol yields 3-aminopropyl(1-hydroxybutyl)phosphinic acid hydrochloride, m.p. 154°–160°. Treatment of the hydrochloride with propylene oxide/ethanol or passage through a DOWEX ® 50

W×8 (14–40 mesh) ion-exchange column gives 3-aminopropyl(1-hydroxybutyl)phosphinic acid, m.p. 187°–188°, as a white solid.

EXAMPLE 43

In a manner analogous to that described in Example 42, 3-aminopropyl(1-hydroxyisobutyl)phosphinic acid hydrochloride, m.p. 105° (dec.) and 3-aminopropyl(1-hydroxyisobutyl)phosphinic acid, m.p. 122°–123° are obtained by reaction with isobutyraldehyde at 40°–60° for 1 hour.

EXAMPLE 44

In a manner analogous to that described in Example 42, 3-aminopropyl(1-hydroxyethyl)phosphinic acid hydrochloride, m.p. 153°–154° and 3-aminopropyl(1-hydroxyethyl)phosphinic acid, m.p. 255°–256° may be obtained by reaction with acetaldehyde at 0°–15° for 1 hour.

EXAMPLE 45

In a manner analogous to that described in Example 42, 3-aminopropyl(1-hydroxybenzyl)phosphinic acid hydrochloride, m.p. 173°–174° and 3-aminopropyl(1-hydroxybenzyl)phosphinic acid, m.p. 139°–140° are obtained by reaction with freshly distilled benzaldehyde at 40°–60° for 1 hour.

EXAMPLE 46

In a manner analogous to that described in Example 42, 3-aminopropyl(1-hydroxy-4,4,4-trifluoro-butyl)phosphinic acid hydrochloride, m.p. 139,5°–140° and 3-aminopropyl(1-hydroxy-4,4,4-trifluorobutyl)phosphinic acid, m.p. 226°–227° are obtained by reaction with 4,4,4-trifluorobutanal at 20° for 1 hour.

EXAMPLE 47

In a manner analogous to that described in Example 42, 3-aminopropyl[1-hydroxy-(Z)-2-fluoro-but-2-enyl]phosphinic acid hydrochloride, m.p. 110°–112° and 3-aminopropyl(1-hydroxy-2-fluoro-(Z)but-2-enyl)phosphinic acid, m.p. 121°–122° are obtained by reaction with (Z)-2-fluorocrotonaldehyde at 0° (very exothermic) for 1 hour.

EXAMPLE 48

In a manner analogous to that described in Example 42, 3-aminopropyl(1-hydroxy-1-cyclopropylmethyl)phosphinic acid hydrochloride, m.p. 135°–136° and 3-aminopropyl(1hydroxy-1-cyclopropylmethyl)phosphinic acid, glass: δ($^1$H-NMR, $D_2O$); 2.90 (3 H, d and t. CHOH, $CH_2NH_2$), 1.77 (4 H, m), 0.89 (2 H, m, CH). 0.49 (2 H, m, $CH_2$), 0.22 (2 H. m, $CH_2$) are obtained by reaction with 1-formyl cyclopropane at 20° for 1 hour.

EXAMPLE 49

In a manner analogous to that described in Example 42, 3-aminopropyl[1-hydroxy-1-(2-methylthiocyclopropyl)methyl]phosphinic acid hydrochloride, m.p. 100° (dec.) and 3-aminopropyl[1-hydroxy-1-(2-methylthiocyclopropyl)methyl]phosphinic acid, m.p. 105°–106° may be obtained by reaction with 1-formyl-1-methylthiocyclopropane at 40°–60° for 1 hour.

EXAMPLE 50

In a manner analogous to that described in Example 42, 3-aminopropyl(1-hydroxy-1-cyclobutylmethyl)phosphinic acid bydrochloride, m.p. 167°–168° and 3-aminopropyl(1-hydroxy-1-cyclobutylmethyl)phosphinic acid, m.p. 225°–226° are obtained by reaction with 1-formylcyclobutane at 40°–60° for 1 hour.

EXAMPLE 51

A suspension of 2.46 g of 3-aminopropylphosphonous acid in 20 ml of hexamethyldisilazane is heated to reflux under an inert gas for 24 hours after which a clear solution results. The excess hexamethyldisilazane is removed by distillation at atmospheric pressure under a slight positive pressure of inert gas to afford a colourless oil. The oil is cooled to circa 40° and treated with 0.64 g of anhydrous zinc iodide and 25 ml of 1,2-epoxybutane. An exothermic reaction occurs and the epoxybutane refluxes. Reflux is continued for 6 hours after which time thin layer chromatography indicates the reaction to be complete. The reaction mixture is filtered and the filtrate evaporated to dryness in vacuo at 40°. The residue is dissolved in water and stirred at room temperature for 1 hour and the water removed in vacuo to give an oily solid. This is dissolved in some 2.0M aqueous hydrochloric acid and washed with dichloromethane and ether. Removal of the water at 40° in vacuo affords a brown solid which is purified by ion-exchange chromatography on DOWEX ® 50 W×8 (14–40 mesh) to give 3-aminopropyl(-2-hydroxybutyl)phosphinic acid, m.p. 184°–185°. as a white solid.

EXAMPLE 52

In a manner analogous to that described in Example 51, 3-aminopropyl[2-(R)-hydroxy-3-methylbutyl]phosphinic acid, m.p. 187°–189° is obtained by reaction with (R)-(-)-1,2-epoxy-3-methylbutane at 70°.

EXAMPLE 53

A suspension of 2.46 g of 3-aminopropylphosphonous acid in 20 ml of hexamethyldisilazane is heated to reflux under an inert gas for 24 hours. The resulting clear solution is cooled to 15° and 2.0 ml of cyclobutanone are added. An exothermic reaction ensues. The reaction mixture is stirred until the temperature drops to room temperature (approximately 1 hour). Water is added and the volatile materials are removed in vacuo to yield a semi-solid. This is dissolved in 2.0M aqueous hydrochloride acid and washed with 2×100 ml of dichloromethane. The aqueous layer is evaporated in vacuo to afford a solid which is passed through a DOWEX ® 50 W×8 (14–40 mesh) ion-exchange column to give 3-aminopropyl(1-hydroxycyclobutyl)phosphinic acid, m.p. 174°–175° (dec).

EXAMPLE 54

A mixture of 3.0 g of 3-eminopropyl(benzyl)phosphinic acid hydrochloride and 0.6 g of Nishimura catalyst in 30 ml of methanol is hydrogenated during 4 hours. The catalyst is filtered off and the solvent removed by evaporation. The residue is dissolved in 20 ml of methanol and 10 ml of propyleneoxide are added to the solution. Stirring for 3 hours affords a white solid which is filtered off and dried over phosphorous pentoxide to yield 3-aminopropyl(cyclohexylmethyl)phosphinic acid, m.p. 30° (dec.).

EXAMPLE 55

A solution of 1 g of 3-aminopropyl(but-3-enyl)phosphinic acid in 25 ml of water is treated with 0.1 g of 5% palladium on charcoal and hydrogenated at room temperature until hydrogen uptake ceases. The catalyst is removed by filtration of the reaction mixture through celite and the filtrate evaporated to dryness, to afford 3-aminopropyl(butyl)phosphinic acid, m.p. 231°–234° (dec.) $^{31}$-NMR (D$_2$O): δ+44.6 ppm.

EXAMPLE 56

A suspension of 25.7 g of 3-(N-benzyloxycarbonylaminopropyl)phosphonous acid in 150 ml of anhydrous dichloromethane is cooled to 5° under an inert gas and 11.1 g of triethylamine is added. A slight exotherm results and all the solid dissolves. The solution is re-cooled to 0° and a solution of 11.94 g of ethyl chloroformate in 100 ml of anhydrous dichloromethane is added dropwise over 15–30 minutes, maintaining the temperature at 10°. The reaction is exothermic and gas evolution together with the formation of a white precipitate is observed. The white suspension is stirred for 1 hour at room temperature, diluted with 500 ml of dichloromethane and washed with 2×200 ml of water. After drying the organic phase with anhydrous magnesium sulfate and evaporation of the solvent in vacuo 3-(N-benzyloxycarbonylaminopropyl)phosphonous acid ethyl ester is obtained as a colourless viscous oil; $^1$H-NMR: δ(CDCl$_3$); 7.35 (5 H, m, Ph), 7.13 (1 H, d, J=530 Hz, P-h), 5.08 (2 H, m, CH$_2$Ph), 4.13 (2 H, m, P—OCH$_2$), 3.27 (2 H, brd, sharpens on D$_2$O addition, CH$_2$, NH$_2$), 1.82 (4 H, m, 2×CH$_2$), 1 35 (3 H, t, CH$_3$)

A solution of 2.85 g of 3-(N-benzyloxycarbonylaminopropyl)phosphonous acid ethyl ester in 25 ml of anhydrous tetrahydrofuran is cooled to 0° under an inert gas and 2.22 g of triethylamine added followed by dropwise addition of a solution of 2.39 g of trimethylsilylchloride in 25 ml of anhydrous tetrahydrofuran over 15 minutes. A slight exotherm reaction occurs and a white precipitate is observed. The suspension is stirred at room temperature for 20 hours and filtered under inert gas. The solid is washed with a further 50 ml of anhydrous tetrahydrofuran under inert gas and the combined organic filtrate evaporated to dryness in vacuo to afford a slightly cloudy colourless oil. This oil is treated with 10–15 ml of freshly distilled n-butyraldehyde maintaining an inert atmosphere. An exothermic reaction ensues, the temperature rising circa 35°. The mixture is allowed to cool to room temperature, is diluted with 100 ml of dichloromethane and washed with water, 0.1 ml of aqueous hydrochloride acid followed by water. Drying of the solvent and removal of the dichloromethane in vacuo yields ethyl 3-(N-benzyloxycarbonylaminopropyl)(1-hydroxybutyl)phosphinate a: a mixture of diastereoisomers; $^1$H-NMR: δ (CDCl$_3$); 7.35 (5 H, m), 5.10 (1 H, n), 4.25–3.98 (1 H, m, CHOH), 3.28 (2 H, t, CH$_2$NH$_2$), 1.97–1.44 (4 H, m), 1.40–1.21 (4 H, m), 0.95 (3 H, t, CH$_3$)

A solution of 0.714 g of ethyl 3-(N-benzyloxycarbonylaminopropyl)-(1-hydroxybutyl) phosphinate in 10 ml of anhydrous dichloromethane at room temperature is treated with 0.712 g of N,N'-thiocarbonyldiimidazole. The red solution is stirred for 20 hours at room temperature, diluted with dichloromethane and washed with cold 1.0m aqueous hydrochloric acid (2×30 ml), water and saturated aqueous sodium bicarbonate solution. The organic layer is dried and the solvent removed in vacuo to afford ethyl 3-(N-benzyloxycarbonylaminopropyl)-[1-(0-thiocarbonylimidaz-1-oyloxy)-butyl]phosphinate as a pale yellow oil: $^1$H-NMR: δ (CDCl$_3$); 8.46 (1 H, d, t), 7.47 (1 H, d, t), 7.35 (5 H, m, Ph), 7.07 (1 H, m), 6.12 (1 H, m, CHO), 5.10 (2 H, CH$_2$Ph), 4.25–3.98 (2 H, m, CH$_2$OP), 3.25 (2 H, t, CH$_2$NH$_2$), 1.97–1.44 (2 H, m, 2×CH$_2$), 1.42–1.20 (4 H, m), 0.96 (3 H, t, CH$_3$)

A solution of ethyl 3-(N-benzyloxycarbonylaminopropyl)-[1-(0-thiocarbonylimidaz-1-oyloxy)butyl]phosphinate in 10 ml of anhydrous degassed benzene is treated with 0.291 g of tri-n-butyltin hydride. The clear solution is brought to reflux and 0.08 g of azobisisobutyronitrile added. Reflux is continued for 1 hour after which time thin layer chromatography indicates the reaction to be complete. The reaction is cooled to room temperature and the volatile material removed in vacuo to afford a pale yellow oil. The oil is partitioned between acetonitrile methane and the acetonitrile layer separated and washed with a further 2×20 ml hexane. Evaporation of the acetonitrile in vacuo and chromatography of the residual oil on silica gel affords ethyl 3-(N-benzyloxycarbonylaminopropyl)(n-butyl)phosphinate as an oil; saponification of this oil with lithium hydroxide followed by acidification with phosphoric acid affords 3-(N-benzyloxycarbonylamino)propyl(n-butyl)phosphinic acid m.p. 116°–118° described in example 3 yillding 3-aminopropyl(n-butyl)phosphinic acid, m.p. 231°–234° (dec.).

EXAMPLE 57

A mixture of 2.0 g ethyl 3-aminopropyl(1-hydroxybutyl)-phosphinate and 20.0 ml 2M aqueous hydrochloric acid is refluxed for 2 hours and then evaporated to dryness. The residual oil is dissolved in 10 ml of water, and re-evaporated. The residue is dissolved in 20 ml of ethanol and treated with propylene oxide and to give 1.5 g of 3-aminopropyl(1hydroxybutyl)phosphinic acid, m.p. 188°.

The starting material is prepared as follows:

A mixture of 24.5 g ethyl-(1,1-diethoxyethyl)phosphinate and 40 g of hexamethyldisilazane are heated at 148° under a inert gas for 3 hours. The reaction mixture is cooled to room temperature and 6 g of acrylonitrile a added. The mixture is stirred for 2 hours. The reaction mixture is evaporated, dissolved in aqueous methanol and re-evaporated to give 25,7 g of ethyl 2-cyanoethyl(1,1-diethoxyethyl)phosphinate ($^{31}$P-HMR:δ=N 44 ppm).

This oil is treated with 25.7 g of trimethylsilyl chloride in 150 ml of commercial grade chloroform (containing 1 to 5% b.w. of ethanol) at room temperature for 6 hours under argon. The reaction mixture is stripped, the oil is dissolved in methanol and re-evaporated to give ethyl 2-cyanoethylphosphinate.

A mixture of 2.5 g of ethyl 2-cyanoethylphosphinate of 4.96 g of hexamethyl disilazane is treated to 140° for 1 hour. The mixture is cooled to 50° and under 2,45 g of n-butyraldehyde are added. After 15 minutes to mixture is stripped to an oil which is co-evaporated with 10 ml of aqueous ethanol to give 3.7 g ethyl 2-cyanoethyl(1-hydroxybutyl)phosphinate. This oil is dissolved in 50 ml of ethanol containing 0.58 g of ammonia and 0.5 g of Raney Nickel and hydrogenated for 10 hours. The catalyst is filtered off and the solvent is removed by evaporation to give 2.0 g of ethyl 3-aminopropyl(1-bydroxybutyl-n-butyl)phosphinate

EXAMPLE 58

A suspension of 1.23 g 3-aminopropylphosphonous acid in 25 ml of hexamethyldisilazane is heated to reflux under an inert gas for 20 hours. After this time a clear solution results and the reaction mixture is cooled to room temperature under inert gas and 50 ml of anhydrous acetone is added and an exothermic reaction results. The reaction mixture is allowed to cool to room temperature and the volatile components removed in vacuo to afford a clear oil. This oil is dissolved in 50 ml of a 2.0M hydrochloric acid solution in water and washed with 2×100 ml of dichloromethane and 1×100 ml of ether. The aqueous layer is evaporated to dryness to give a semi-solid residue which is co-evaporated with water (10×20 ml) and absolute ethanol (10×20 ml) yielding 3-aminopropyl(2-hydroxyprop-2-y)phosphinic acid hydrochloride m.p. 159°–161° as a white solid. This is suspended in absolute ethanol and treated with propylene oxide. Filtration and drying of the solid affords 3-aminopropyl(2-hydroxyprop-2-yl)phosphinic acid; m.p. 243°–244°.

EXAMPLE 59

In a manner analogous to that described (above) in Example 58 3-Aminopropyl-(1,2-dihydroxyprop-2-yl)phosphinic acid hydrochloride, m.p. 175°–179° and 3-aminopropyl-(1,2-dihydroprop-2-yl)phosphinic acid, m.p. 209°–210° (dec.) may be obtained by reaction with 1-0-tertbutyldimethylsilyloxymethyl propan-2-one at 70° for 20 hours.

The starting material may be obtained as follows:

To a solution of 6.8 g of imidazole in 20 ml of anhydrous dimethylformamide is added 7.5 g of tert-butyldimethylsilyl chloride in the same solvent at 10° under inert gas. The clear solution is stirred for 15 minutes at 10° before addition of 20 ml of an anhydrous dimethylformamide solution of 3.7 g of hydroxy acetone. A slight exothermic reaction ensues and the reaction mixture is warmed to room temperature and stirred for 16 hours. Subsequently the reaction mixture is diluted with ether and washed with water. After drying the organic phase with anhydrous magnesiumsulphate and removal of the ether in vacuo the clear oil is distilled to afford 1-0-tert-butyldimethylsilyloxymethyl propan-2-one; b.p. 84°–85°/18 mm Hg.

EXAMPLE 60

In an analogous fashion to that described in Example 51, 3-amino-2-hydroxy-propyl(n-propyl)phosphinic acid and its hydrochloride can be prepared by reaction of n-propylphosphonous acid ethyl ester with epoxypropylphthalimide.

EXAMPLE 61

In a manner analogous to that described in Example 9, 3-amino-2-(p-chlorophenyl)-propyl(n-propyl)phosphinic acid and its hydrochloride can be prepared by reaction of n-propylphosphonous acid ethyl ester with 1-phthalimido-2-(p-chlorophenyl)-3-bromo-propane.

EXAMPLE 62

In a manner analogous to that described in Example 42, 3-amino-1-hydroxy-propyl(n-propyl)phosphinic acid and its hydrochloride can be prepared by reaction of 3-(benzyloxycarbonylamino)propanal with n-propylphosphonousacid ethyl ester.

EXAMPLE 63

In a manner analogous to that described in Example 32, 3-aminopropyl(4-hydroxybutyl)phosphinic acid and its hydrochloride can be obtained from the reaction of 3-aminopropylphosphonous acid and 4-hydroxybut-1-ene. Also, by the same method, 3-aminopropyl(3-hydroxybutyl)phosphinic acid and its hydrochloride can be obtained by reaction of 3-aminopropylphosphonous acid and 3-hydroxybut-1-ene.

EXAMPLE 64

In a manner analogous to that described in Example 9, 3aminopropyl[2-(S)-methylbutyl]phosphinic acid, m.p. 252°–255° (dec.)

$[\alpha]^{20}_{365\ nm} = +20.5°$; $[\alpha]^{20}_{436\ nm} = +13.8°$;

$[\alpha]^{20}_{546\ nm} = +8°$; $[\alpha]^{20}_{578\ nm} = +6.6°$; and $[\alpha]^{20}_{589\ nm} = +6.1°$ ($c = 0.95$ in water)

is obtained by reaction with (S)-(+)-2-methylbutyliodide at 120°, 16 hours.

is obtained by reaction with (S)-(+)-2-methylbutyliodide at 120°, 16 hours.

EXAMPLE 65

A suspension of 2.46 g of 3-aminopropylphosphonous acid in 20 ml of hexamethyldisilazane is heated to reflux under an inert atmosphere for 24 hours after which a clear solution results. The excess hexamethyldisilazane is removed by distillation at atmospheric pressure under a slight positive pressure of inert gas to afford a colourless oil. The oil is cooled to circa 66° and treated with 0.64 g of anhydrous zinc iodide and 4.62 g of N-(2,3-epoxypropyl)phthalimide. An exothermic reaction occurs. The reaction mixture is refluxed for 6 hours after which time thin layer chromatography indicates the reaction to be complete. The reaction mixture is filtered and the filtrate evaporated to dryness in vacuo at 40°. The residue is dissolved in water and stirred at room temperature for 1 hour and the water removed in vacuo to give an oily solid. This is dissolved in 25 ml of 2.0M aqueous hydrochloric acid and washed with dichloromethane and ether. Removal of the water at 40° in vacuo affords a brown solid which is purified by ion-exchange chromatography on DOWEX® 50 W ×8 (14–40 mesl) to give 3-aminopropyl(2-hydroxy-3-phthalimido-propyl) phosphinic acid, m.p. 268°–71°, as a white solid.

This can be converted into 3-aminopropyl(3-amino-2-hydroxy-propyl)phosphinic acid by methods known per se.

EXAMPLE 66

A suspension of 2.46 g of 3-aminopropylphosphonous acid in 20 ml of hexamethyldisilazane is heated to reflux under an inert gas for 24 hours. The resulting clear solution is cooled to room temperature and 14.4 g of freshly distilled methyl vinyl ketone are added. An exothermic reaction ensues, the reaction temperature rising to approximately 60° C. The reaction mixture is stirred for 1 hour at a temperature between 50° and 60°. After cooling to room temperature, the volatile materials are removed in vacuo to yield a colourless oil. This oil is dissolved in water and stirred at room temperature for 1 hour and the aqueous layer is evaporated to dryness at 55°. A semi-solid residue is obtained which is dissolved in 50 ml of 2.0M aqueous hydrochloric acid and washed with dichloromethane, (3×100 ml), and ether (1×100 ml). After removal of the water, the white solid is co-evaporated with water (10×50 ml) and then with absolute ethanol (10×50 ml). Crystallisation of the residue form ethanol yields 3-aminopropyl(3-oxobutyl)-phosphinic acid hydrochloride. Treatment of the hydrochloride with propylene oxide/ethanol or passage through a DOWEX ® 50 W×8 (14×40 mesh) ion-exchange column gives 3-aminopropyl(3-oxobutyl)phosphinic acid, m.p. 163°-5° (decomp.), as a white solid.

EXAMPLE 67

A suspension of 1.3 g of ethyl 3-(N-benzyloxycarbonylamino)-1-hydroxy-propyl(n-butyl) phosphinate in 10 ml of concentrated aqueous hydrochloric acid is heated to reflux for 20 hours. The clear solution is cooled to room temperature and washed with 1×50 ml of dichloromethane and 1×50 ml of ether. Evaporation of the aqueous layer affords a solid which is co-evaporated with 5×50 ml of water and 5×50 ml of absolute ethanol. Drying of the solid and crystallisation from ethanol affords 3-amino-1-hydroxy-propyl(n-butyl)phosphinic acid hydrochloride, m.p. 147°-150°. Dissolution of the hydrochloride salt in ethanol and treatment with propylene oxide affords, after filtration and drying, 3-amino-1-hydroxy-propyl(n-butyl)phosphinic acid, m.p. 123°-125°.

The starting materials may be prepared as follows.

A mixture of 1.50 g of ethyl (n-butyl)phosphinate, 1.01 g triethylamine and 2.07 g 3-(N-benzyloxycarbonylamino)propionaldehyde is heated to 100° C. for 4 hours. After this time the mixture is cooled to 20° and the volatile components are removed in high vacuum. Chromatography of the residue on silica gel affords ethyl 3-(N-benzyloxycarbonylamino)-1-hydroxy-propyl(n-butyl)phosphinate as a viscous oil.

EXAMPLE 68

A solution of 6.4 g of ethyl 3-phthalimido-2-trimethyl-silyloxy-propyl (ethyl)phosphinate in 100 ml of concentrated aqueous hydrochloric acid is heated to reflux for 20 hours. After this time the suspension is cooled to room temperature and filtered. The filtrate is evaporated to dryness, the resulting semi-solid is co-evaporated with water (5×50 ml) and absolute ethanol (5×100 ml) and the white solid is dried in high vacuum overnight. Crystallisation from absolute ethanol/acetone affords 3-amino-2-hydroxy-propyl(ethyl)phosphinic acid hydrochloride, m.p. 114°-115°.

The starting material may be obtained as follows:

A solution of 21.0 g of ethyl 1,1-diethoxyethylphosphinate in 50 ml of anhydrous tetrahydrofuran is added dropwise to a suspension of 4.36 g of sodium hydride (55% dispersion in oil) in 150 ml of anhydrous tetrahydrofuran under an inert atmosphere maintaining the temperature at 15° C. After addition is complete the resulting suspension is stirred for 1 hour at 20° C. before re-cooling to 15° and addition of 86 g of ethyl bromide in 50 ml anhydrous tetrahydrofuran.

The suspension is stirred for 16 hours at 20° C. and water (50 ml) is carefully added. After concentration in vacuo, the residue is dissolved in water and extracted with dichloromethane. The organic layer is separated and dried over anhydrous magnesium sulphate. Removal of the solvent in vacuo affords ethyl 1,1-diethoxyethyl(ethyl)phosphinate as a colourless oil; b.p. 80° at $4 \times 10^{-2}$ mbar.

A suspension of 19.14 g of ethyl 1,1-diethoxyethyl(ethyl)phosphinate in 100 ml of 4.0M aqueous hydrochloric acid is heated to reflux for 20 hours. After cooling to 20° the solution is washed with dichloromethane followed by ether. Evaporation of the aqueous layer and coevaporation of the oily residue with 5×100 ml of water and 5×100 ml absolute alcohol affords ethyl phosphonous acid.

A solution of 7.63 g of ethyl phosphonous acid in 150 ml of anhydrous dichloromethane is cooled to 0° under an inert atmosphere and triethylamine added dropwise. To the resulting cloudy solution are added, at 0°, 8.81 g of ethyl chloroformate in 50 ml of anhydrous dichloromethane. The reaction becomes exothermic and vigorous gas evolution occurs. After warming to room temperature, the mixture is diluted with 100 ml of dichloromethane and washed with 2×100 ml of water. Drying and removal of the solvent in vacuo affords ethyl ethylphosphinate as a colourless oil.

A mixture of 4.55 g of anhydrous triethylamine and 5.0 g of ethyl ethylphosphinate in 100 ml of anhydrous tetrahydrofuran under an inert atmosphere is treated with 4.89 g of chlorotrimethylsilane. The resulting suspension is stirred for 20 hours at room temperature and the solid removed by filtration. Concentration in vacuo affords a cloudy, colourless oil which is treated with 5.10 g of anhydrous N-(2,3-epoxypropyl)phthalimide and 1.0 g of anhydrous zinc chloride. The mixture is heated to 66° C. under an inert atmosphere for 3 hours, cooled to 20° and diluted with dichloromethane. The organic solution is washed with 100 ml of a 10% aqueous sodium bicarbonate solution and dried over anhydrous magnesium sulphate. Removal of the solvents and chromatography on silica gel affords ethyl 3-phthalimido-2-trimethylsilyloxy-propyl(ethyl)phosphinate as a viscous oil.

EXAMPLE 69

3-Aminopropyl(2-methoxyethyl)phosphinic acid ×0.13 H₂O, m.p. 208°-212° (hydrochloride: m.p. 114°-115°) is obtained from 3-aminopropylphosphonous acid, hexamethyldisilazane, N-ethyl-N,N-diisopropylamine and 2-chloroethyl methyl ether at 120° for 48 hours.

EXAMPLE 70

3-Aminopropyl(2-ethoxymethyl)phosphinic acid ×0.26 H₂O, m.p. 220°-225° (dec hydrochloride: oil) is obtained from 3-aminopropylphosphonous acid, hexamethyldisilazare, N-ethyl-N,N-diisopropyl-amine and chloromethyl-ethylether at 25° for 120 hours.

EXAMPLE 71

A mixture of 1.4 g (5.8 mMol) of ethyl 3-aminopropyl(1,1-difluorobutyl)phosphinate and 15 ml cf 12M hydrochloric acid is stirred for 8 hours at 80° C. The reaction mixture is evaporated to dryness and the residue is recrystallized from ethanol/ether giving 3-aminopropyl(1,1-difluorobutyl) phosphinic acid hydrochloride, m.p. 149°-151° C.

The starting material may be obtained as follows:

To a suspension of 15.8 g of sodium hydride (dispersion in oil) in 500 ml of tetrahydrofuran are added dropwise 67 g (300 mMol) of ethyl 1,1-diethoxyethylphosphinate at such a rate so that the temperature does not exceed 25° C. This mixture is stirred for one hour at room temperature, then cooled to −10° C. and 77.8 g (900 mMol) of chlorodifluoromethane are introduced. Stirring is continued for another 2 hours at room temperature, then 100 ml of ice-cold water are added. The mixture is extracted three times with dichloromethane and the combined extracts dried over magnesium sulphate. Removal of the solvent in vacuo gives ethyl 1,1-diethoxyethyl(difluoromethyl)phosphinate as a viscous oil, Rf=0.44 (CH$_2$Cl$_2$/CH$_3$COOH, 9+1).

To a solution of 15.6 g (60 mMol) of ethyl 1,1-diethoxyethyl(difluoromethyl)phosphinate in 150 ml of dry tetrahydrofuran is slowly added at −65° C. with stirring under argon 48.8 ml (78 mMol) of n-butyllithium (1.6 moles in hexane). This mixture is stirred for additional 15 minutes at this temperature. Still at −65° C., 71 ml (78 mMol) of n-propylbromide are added dropwise and then the reaction mixture is allowed to warm to 0° C. and stirring is continued for 1 hour.

Water is added and the mixture is extracted three times with ether. The organic layer is washed once with water dried over magnesium sulphate and evaporated giving a yellow oil. This is chromatographed on 600 g of silica gel eluting with ether. The product-containing fractions are collected and the solvent is evaporated to leave pure ethyl 1,1-diethoxyethyl(1,1-difluorobutyl)phosphinate, Rf=0.5 (CH$_2$Cl$_2$/CH$_3$COOH, 9+1).

To 8.2 g (27.1 mMol) of ethyl 1,1-diethoxyethyl(1,1-difluorobutyl)phosphinate in 81 ml of dry tetrahydrofuran are added, with stirring at room temperature, 9 ml of ethanol and 5.1 ml (40.7 mMol) of trimethylchlorosilane. After 5 hours of stirring the reaction mixture is evaporated and the remaining oil is chromatographed on a silica gel column eluting with ether. The product-containing fractions are collected and the solvent is evaporated leaving 1,1-difluorobutylphosphonous acid ethyl ester as colorless oil, Rf=0.4 (CH$_2$Cl$_2$/CH$_3$COOH, 95+5).

280 mg (12 mMol) of sodium is dissolved in 17 ml of dry ethanol. This solution is cooled to −10° C. and 4.5 g (24.2 mMol) of 1,1-difluorobutylphosphonous acid ethyl ester and 1.6 ml (24.2 mMol) of acrylonitrile are added with stirring.

The reaction mixture is allowed to warm to room temperature and stirring is continued for 20 hours. The mixture is treated with glacial acetic acid and evaporated to dryness. The residue is dissolved in dichloromethane, washed twice with water, dried with magnesium sulphate and evaporated, giving ethyl 2-cyanoethyl(1,1-difluorobutyl)phosphinate as an oil, Rf: 0.32 (CH$_2$Cl$_2$/CH$_3$COO, 9+1).

3.2 g (13.4 mMol) of ethyl 2-cyanoethyl(1,1-difluorobutyl)phosphinate are dissolved in 100 ml of dry ethanol and 10 g of liquid ammonia and 1 g of Raney-nickel are added. This mixture is hydrogenated at 50° C. and 100 bar hydrogen pressure for 3 hours.

The reaction mixture is filtered and the solvent removed under vacuum. After distillation of the oily the residue in a Kugelrohrofen at 130° C. and 2·10$^{-3}$ mbar, there is obtained ethyl 3-aminopropyl(1,1-difluorobutyl)phosphinate Rf: 0.22 (CH$_2$Cl$_2$/MeOH/NH$_3$ 90+9+1).

EXAMPLE 72

The solution of 2.4 g of ethyl 3-phthalimido-2-trimethylsilyloxy-propyl(n-butyl)phosphinate in 50 ml of concentrated aqueous hydrochloric acid is heated to reflux for 20 hours. After this time the suspension is cooled to room temperature and filtered. The filtrate is evaporated to dryness and the resulting semi-solid is co-evaporated with water (5×50 ml) and absolute ethanol (5×100 ml) and the white solid dried in high vacuum overnight. Crystallisation from absolute ethanol affords 3-amino-2-hydroxy-propyl(n-butyl)phosphinic acid hydrochloride, m.p. 158°-160°.

The starting material may be obtained as follows:

A solution of 52.55 g of ethyl-1,1-diethoxyethylphosphinate in 50 ml of anhydrous tetrahydrofuran is added dropwise to a suspension of 12 g of sodium hydride (55% dispersion in oil) in 50 ml anhydrous tetrahydrofuran under an inert atmosphere maintaining the temperature at 15° C.

After addition is complete, the resulting suspension is stirred for 1 hour at 20° C. before re-cooling to 15° and addition of 102.8 g n-butylbromide.

The suspension is stirred for 16 hours at 20° C. and water (50 ml) is carefully added. After concentration in vacuo the residue is dissolved in water/dichloromethane and extracted.

The organic layer is separated and dried with anhydrous magnesium sulphate. Removal of the solvent in vacuo affords ethyl 1,1-diethoxyethyl(n-butyl)phosphinate as a colourless oil.

A solution of 176 g of ethyl 1,1-diethoxyethyl(n-butyl)phosphinate in 540 ml of absolute dichloromethane containing 10% of absolute ethanol is treated with 143.6 g of trimethylchlorosilane. After stirring for 48 hours at room temperature, the solvent is removed in vacuo to afford a pale yellow oil. Distillation in vacuo affords ethyl n-butyl-phosphinate, b.p. 27°-34° (2×10$^{-2}$ mbar).

A mixture of 3.79 g of anhydrous triethylamine and 4.5 g ethyl n-butylphosphinate in 100 ml of anhydrous tetrahydrofuran under an inert atmosphere is treated with 4.07 g of trimethylchlorosilane. The resulting suspension is stirred for 20 hours at room temperature and the solid removed by filtration. Concentration in vacuo affords a cloudy, colourless oil which is treated with 6.09 g of anhydrous N-(2,3-epoxypropyl)phthalimide and 0.5 g of anhydrous zinc chloride. The mixture is heated to 66° C. under an inert atmosphere for 3 hours, cooled to 20° and diluted with dichloromethane. The organic solution is washed with 100 ml 10% of aqueous sodium bicarbonate solution and dried over anhydrous magnesium sulphate. Removal of the solvent and chromatography on silica gel affords ethyl 3-phthalimido-2-trimethylsilyloxy-propyl(n-butyl)phosphinate as a viscous oil.

EXAMPLE 73

A mixture of 1.23 g (10 mMol) of 3-aminopropyl-phosphonous acid and 8.07 g (50 mMol) of hexamethyldisilazane is refluxed under an atmosphere of argon with stirring for 16 hours to give a solution. To this solution are added at reflux 5 ml of diethyleneglycol dimethyl ether and the reaction mixture is refluxed for additional 2 hours.

The reaction mixture is then cooled to 100° and 1.94 g (15 mMol) of N-ethyl-N,N-diisopropyl-amine is added during 10 minutes followed by addition of 3.78 g (15 mMol) of 4,4,4-trifluoro-3-methyl-1-iodo-butane.

The reaction mixture is heated with stirring at 150° for 22 hours. After cooling to 10°, the white precipitate is filtered off and the filtrate is evaporated under reduced pressure. The clear solution is cooled, diluted with dichloromethane (30 ml) and extracted with 2N hydrochloric acid (3×15 ml).

The combined hydrochloric acid extracts are evaporated in vacuo to dryness and co-evaporated with water (2×15 ml) to give a white solid which is dissolved in 20 ml of methanol. Then 150 ml of propylene oxide are added. After standing overnight at 4°, a white solid precipitates. The precipitate is collected by filtration to give 3-aminopropyl(4,4,4-trifluoro-3-methyl-butyl)-phosphinic acid, m.p. 245°–250° (dec.)

The crude material is chromatographed on 35 g Opti-Up ® $C_{12}$ eluting with water. The product-containing fractions are collected and evaporated in vacuo to dryness.

After recrystallisation from methanol diethylether give pure 3-amino-propyl-(4,4,4-trifluoro-3-methyl-butyl) phosphinic acid of m.p. 255°–258° (dec.)

4,4,4-trifluoro-3-methyl-1-iodo-butane is prepared in the following manner.

To a mixture of 19 g phosphoric acid (98%) and 19 g potassium iodide are added at 40° under stirring 4.75 g (33.4 mMol) of 4,4,4-trifluoro-3-methyl-butan-1-ol over a period of 10 minutes. The mixture is then heated at 120° for 16 hours, a cooling poured into ice-water and extracted with diethylether. The etheric extracts are washed with 10% sodium thiosulfate and brine acid dried over sodium sulphate. After filtration, the solvent is removed through a 15 cm Vigreux-column at atmospheric pressure, followed by fractionation giving 4,4,4-trifluoro-3-methyl-1-iodo-butane, b.p. 76°–77° at 140 mbar.

EXAMPLE 74

In an analogous manner as described in Example 73, also 3-aminopropyl(4,4,4-trifluoro-3-trifluoromethyl-butyl)phosphinic acid can be manufactured.

EXAMPLE 75

A solution of 6.9 g of isobutyl 3-amino-2-(4-chlorophenyl)propyl(methyl)phosphinate in 60 ml of 36% aqueous hydrochloric acid is heated to reflux for a period of 15 hours. The reaction mixture is allowed to cool to room temperature, concentrated under reduced pressure and co-evaporated three times with 25 ml of water under reduced pressure. The crude product is dissolved in 25 ml of water, washed twice with 20 ml of diethyl ether, and the aqueous layer treated with activated charcoal. The charcoal is removed by filtration and the filtrate evaporated under reduced pressure. The crude product is dissolved in 50 ml of ethanol and 2 ml of propylene oxide are added dropwise. The precipitated solid is collected by filtration when free from halogen and dried. Recrystallisation from water then give 3-amino-2-(4-chlorophenyl)-propyl(methyl)phosphinic acid ×1.0 $H_2O$, m.p. 165°–70°, $^{31}P$ N.M.R. spectrum: $\delta = +39.9$ ppm ($D_2O$).

The starting material may be prepared as follows:

To a solution of 1.62 g of diisopropylamine in 20 ml of dry tetrahydrofuran at −78° C. under an atmosphere of nitrogen are added 10.0 ml of a 1.6M solution of n-butyllithium in hexane. This solution is then stirred for a period of 10 minutes at this temperature, after which time a solution of 2.0 g of isobutyl, P,P-dimethyl-phosphinate is added. This mixture is stirred at −78° C. for a period of 1 hour, after which time a solution of 2.45 g of tran-1-(4-chlorophenyl)-2-nitro-ethene in 20 ml of tetrahydrofuran is added. This mixture is then allowed to warm to room temperature when 40 ml of a saturated ammonium chloride solution is added. The aqueous layer is then extracted with 2×25 ml of diethyl ether and the organic extracts are combined and dried over magnesium sulphate. The solvent is then evaporated under reduced pressure and the crude product purified by chromatography on silica gel using 5 parts ethyl acetate to 1 part ethanol as eluent. The fractions containing product are combined and concentrated under reduced pressure to give isobutyl 2-(4-chlorophenyl)-3-nitro-propyl-(methyl)phosphinate as a viscous oil; $^{31}P$ N.M.R. spectrum: $\delta = +50.5$ and $+50.1$ ppm ($CDCl_3$).

A solution of 6.8 g of isobutyl 2-(4-chlorophenyl)-3-nitro-propyl(methyl)phosphinate in 80 ml of ethanol is added to 64 g of an 8% solution of ammonia in ethanol. To this are added 8 ml of Raney Nickel slurry and the resulting mixture is hydrogenated at 1 bar until hydrogen uptake ceases. The mixture is then filtered and the filtrate is concentrated under reduced pressure to give isobutyl 3-amino-2-(4-chlorophenyl)-propyl(methyl)-phosphinate as a viscous oil, $^{31}P$ N.M.R. spectrum: $\delta = +54.0$ and $+53.4$ ppm ($CDCl_3$).

EXAMPLE 76

A solution of 11.8 g of isobutyl 3-amino-2-(4-fluorophenyl)-propyl-(methyl)phosphinate in 60 ml cf 36% aqueous hydrochloric acid is heated to reflux for a period of 15 !ours. The reaction mixture is allowed to cool to room temperature, concentrated under reduced pressure and co-evaporated three times with 25 ml of water under reduced pressure. The crude product is dissolved in 25 ml of water, washed twice with 20 ml of diethyl ether, and the aqueous layer treated with activated charcoal. The charcoal is removed by filtration and the filtrate evaporated under reduced pressure. The crude product is dissolved in 50 ml of ethanol and 1-2 ml of propylene oxide is added dropwise. The precipitated solid is collected by filtration when free from halogen and dried. Recrystallisation from water then give 3-amino-2-(4-fluorophenyl)-propyl(methyl)phosphinic acid ×1.0 $H_2O$, m.p. 215°–220°, $^{31}P$ N.M.R. spectrum: $\delta = +39.8$ ppm ($D_2O$).

The starting material may be prepared as follows:

To a solution of 8.1 g of diisopropylamine in 50 ml of dry tetrahydrofuran at −78° C. under an atmosphere of nitrogen are added 50.0 ml of a 1.6M solution of n-butyllithium in hexane. This solution is then stirred for a period of 10 minutes at this temperature, after which time a solution of 10.0 g of isobutyl P,P-dimethyl-phosphinate is added. This mixture is stirred at −78° C. for a period of 1 hour, after which time a solution of 11.1 g of trans-1-(4-fluorophenyl)-2-nitro-ethene in 50 ml of tetrahydrofuran is added. This mixture is then allowed to warm to room temperature when 40 ml of a saturated ammonium chloride solution is added: The aqueous layer is then extracted with 2×25 ml of diethyl ether and the organic extracts are combined and dried over magnesium sulphate. The solvent is then evaporated under reduced pressure and the crude product purified by chromatography on silica gel using 5 parts ethyl acetate to 1 part ethanol as eluent. The fractions containing product are combined and concentrated under reduced pressure to give isobutyl 2-(4-fluorophenyl)-3-nitro-propyl-(methyl)phosphinate as a viscous oil, $^{31}P$-N.M.R. spectrum: $\delta = +51.0$ and $+50.6$ ppm ($CDCl_3$).

A solution of 11.6 g of isobutyl 2-(4-fluorophenyl)-3-nitro-propyl (methyl)phosphinate in 100 ml of ethanol is added to 114 g of a 8% solution of ammonia in ethanol. To this are added 9 ml of Raney Nickel slurry and the resulting mixture is hydrogenated at 1 bar until hydrogen uptake ceases. The mixture is then filtered and the filtrate is concentrated under reduced pressure to give isobutyl 3-amino-2-(4-fluorophenyl)-propyl-(methyl)-phosphinate as a viscous oil, $^{31}P$ N.M.R. spectrum: $\delta = +54.0$ and $+53.4$ ppm ($CDCl_3$).

EXAMPLE 77

A suspension of 2.46 g of 3-aminopropylphosphonous acid in 20 ml of hexamethyldisilazane is heated to reflux under an inert gas for 24 hours after which a clear solution results. The excess hexamethyldisilazane is removed by distillation at atmospheric pressure under a slight positive pressure of inert gas to afford a colourless oil. The oil is cooled to circa 40° and treated with 0.64 g of anhydrous zinc iodide and 25 ml of (S)-(+)-1,2-exoxy-3-methyl-butane. An exothermic reaction occurs and the epoxybutane refluxes. Reflux is continued for 6 hours after which time thin layer chromatography indicates the reaction to be complete. The reaction mixture is filtered and the filtrate evaporated to dryness in vacuo at 40°. The residue is dissolved in water and stirred at room temperature for 1 hour and the water removed in vacuo to give an oily solid. This is dissolved in some 2.0M aqueous hydrochloric acid and washed with dichloromethane and ether. Removal of the water at 40° in vacuo affords a brown solid which is purified by ion-exchange chromatography on DOWEX® 50 W×8 (14–40 mesh) to give 3-aminopropyl[2-(S)-hydroxy-3-methyl-butyl]phosphinic acid, m.p. 187°–189°, $[\alpha]_D^{20} = -14.5°$.

EXAMPLE 78

A solution of 0.64 g of ethyl 3-(N-tert.-butyloxycarbonylamino)-2-(4-chlorophenyl)-1-hydroxy-propyl (methyl)phosphinate in 12 ml of concentrated aqueous hydrochloric acid is heated to reflux for 5 hours. The mixture is then cooled and evaporated to dryness in vacuo. The residue is repeatedly co-evaporated with methanol until the hydrochloride salt is obtained as a foam. This is dissolved in 50 ml of methanol and treated with 25 ml of propylene oxide after 40 minutes stirring at room temperature a solid precipitates, and the suspension stirred for a further 1½ hours. The solid is collected by filtration washed with propylene oxide and ether and dried the solid is redissolved in methanol at elevated temperature end filtered. Concentration in vacuo and dilution with ether affords a solid which is collected and dried to give 3-amino-2-(4-chlorophenyl)-1-hydroxy-propyl(methyl)phosphinic acid, m.p. 240°–241° C.

The starting material may be obtained as follows:

A solution of 1.46 g of 3-(N-tert.-butyloxycarbonylamino)-2-(4-chlorophenyl)-propionaldehyde, 0.54 g of ethyl methylphosphinate and 0.695 ml of triethylamine is heated to 100° for 2 hours. The reaction mixture is cooled to room temperature and chromatographed on silica gel to give ethyl 3-(N-tert.-butyloxycarbonylamino)-2-(4-chlorophenyl)-1-hydroxy-propyl(methyl)phosphinate.

EXAMPLE 79

A solution of 0.35 g of ethyl 3-(N-tert.-butyloxycarbonylamino)-2-(4-chlorophenyl)-1-hydroxy-propyl (n-butyl)phosphinic acid in 10 ml of 5.0M aqueous hydrochloric acid is heated to reflux for 24 hours. The reaction is cooled to room temperature and washed with 3×50 ml dichloromethane and 1×50 ml ether. After evaporation of the aqueous layer the residue is co-evaporated with water (3×50 ml) and absolute ethanol (3×50 ml) and dried in high vacuum to afford 3-amino-2-(4-chlorophenyl)-1-hydroxy-propyl (n-butyl)phosphinic acid hydrochloride.

The starting material may be prepared as follows:

A material of 283 mg of 3-(N-tert.-butyloxycarbonylamino)-2-(4-chlorophenyl)-propionaldehyde, 150 mg of ethyl n-butyl-phosphinate and 101 mg of triethylamine is heated to 100° C. for 2½ hours. The mixture is cooled to room temperature and the volatile components are removed in high vacuum. Chromatography of the residue on silica-gel affords ethyl 3-(N-tert.-butyloxycarbonylamino)-2-(4-chlorophenyl)-1-hydroxy-propyl-(n-butyl)phosphinate.

EXAMPLE 80

A suspension of 2.46 g of 3-aminopropylphosphonous acid in 20 ml of hexamethyldisilazane is heated to reflux under an inert atmosphere for 24 hours after which a clear solution results. The excess hexamethyldisilazane is removed by distillation at atmospheric pressure under a slight positive pressure of inert gas to afford a colourless oil. The oil is cooled to circa 66° and treated with 0.64 g of anhydrous zinc iodide and 4.62 g of N-(2,3-epoxypropyl)phthalimide. An exothermic reaction occurs. The reaction mixture is refluxed for 6 hours after which time thin layer chromatography indicates the reaction to be complete. The reaction mixture is filtered and the filtrate evaporated to dryness in vacuo at 40°. The residue is dissolved in water and stirred at room temperature for 1 hour and the water removed in vacuo to give an oily solid. This is dissolved in 25 ml of 2.0M aqueous hydrochloric acid and washed with dichloromethane and ether. Removal of the water at 40° in vacuo affords a brown solid which is purified by ion-exchange chromatography on DOWEX® 50 W ×8 (14–40 mesh) to give 3-aminopropyl(2-hydroxy-3-phthalimido-propyl) phosphinic acid, m.p. 268°–71°, as a white solid.

This can be converted into 3-aminopropyl(3-amino-2-hydroxy-propyl)phosphinic acid by methods known per se.

EXAMPLE 81

Preparation of 10,000 tallets each containing 100 mg of the active ingredient with a formula as follows:

| | |
|---|---|
| 3-amino-2-hydroxy-propyl(diethoxy-methyl)phosphinic acid | 1,000.00 g |
| Lactose | 257.00 g |
| Corn starch | 75.00 g |
| Polyethylene glycol 6,000 | 75.00 g |
| Magnesium stearate | 18.00 g |
| Purified water | q.s. |

Procedure: All the powders are passed through a screen with openings of 0.6 mm. Then the drug substance, lactose, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1,2 mm openings and compressed into tablets with 12.8 mm diameter, uppers bisected.

EXAMPLE 82

Preparation of 10,000 capsules each containing 25 mg of the active ingredient with a formula as follows:

| | |
|---|---|
| 3-amino-2-hydroxypropyl(diethoxymethyl)phosphinic acid | 250.0 g |
| Lactose | 1,750.0 g |

Procedure: All the powders are passed through a screen with openings of 0.6 mm. Then the drug substance is placed in a suitable mixer and mixed with the lactose until homogenous. No. 3 capsules are filled with 200 mg using a capsule filling machine.

EXAMPLE 83

In a manner analogous to that described in Examples 81 and 82 tablets and capsules comprising as the active ingredients 10–100 mg of another compounds of the invention, e.g. as described in the Examples 1 to 80.

We claim:

1. A novel process for the manufacture of compounds of the formula

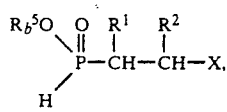 (XV)

wherein $R^{5b}$ denotes a $C_1$–$C_4$ alkyl radical, X denotes cyano, carbamoyl or a group of the formulae —CH($R^3$)—$Z^o$(XVa) or —C($R^3$)=Y (XVb) in which $Z^o$ denotes an acylamino or nitro group, Y denotes an oxo group or an acetalised, thioacetalised, ketalised or thioketalised oxo group, one of $R^1$, $R^2$ and $R^3$ is hydrogen; hydroxy, $C_1$–$C_8$-alkyl, $C_3$–$C_6$-cycloalkyl, phenyl or phenyl substituted by halogen, $C_1$–$C_4$-alkyl, $C_1$–$C_4$-alkoxy and/or trifluoromethyl or $C_7$–$C_{10}$-phenylalkyl or $C_7$–$C_{10}$-phenylalkyl substituted in the phenyl moiety by halogen, $C_1$–$C_4$-alkyl, $C_1$–$C_4$-alkoxy and/or trifluoromethyl, characterised in that a compound of the formula

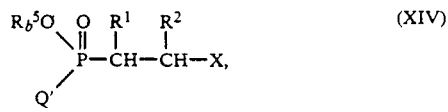 (XIV)

wherein $R^1$, $R^2$, $R^5$ and X are defined hereinabove and Q' denotes a group of the formula —C($R^8$)—C(O$R^9$)(O$R^{10}$)(XIVa) in which $R^8$ denotes hydrogen or lower alkyl and $R^9$ and $R^{10}$, independently of one another, represent lower alkyl or together represent lower alkylene, is treated with an anhydrous protic medium.

* * * * *